United States Patent
Greenberg et al.

(10) Patent No.: US 7,725,191 B2
(45) Date of Patent: May 25, 2010

(54) PACKAGE FOR AN IMPLANTABLE DEVICE

(75) Inventors: Robert J. Greenberg, Los Angeles, CA (US); Joseph H. Schulman, Santa Clarita, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 246 days.

(21) Appl. No.: 11/926,030

(22) Filed: Oct. 28, 2007

(65) Prior Publication Data

US 2008/0077195 A1 Mar. 27, 2008

Related U.S. Application Data

(62) Division of application No. 11/206,484, filed on Aug. 17, 2005, which is a division of application No. 09/515,373, filed on Feb. 29, 2000, now abandoned.

(60) Provisional application No. 60/125,873, filed on Mar. 24, 1999.

(51) Int. Cl.
*A61N 1/375* (2006.01)
(52) U.S. Cl. ...................................................... 607/36
(58) Field of Classification Search .................. 607/2, 607/36, 115
See application file for complete search history.

(56) References Cited

U.S. PATENT DOCUMENTS

| | | | |
|---|---|---|---|
| 2,760,483 A | 8/1956 | Tassicker | |
| 3,699,970 A | 10/1972 | Brindley et al. | |
| 4,041,955 A | 8/1977 | Kelly et al. | |
| 4,628,933 A | 12/1986 | Michelson | |
| 4,666,765 A | 5/1987 | Caldwell et al. | |
| 4,717,581 A | 1/1988 | Robblee | |
| 4,721,551 A | 1/1988 | Byers et al. | |
| 4,819,647 A | 4/1989 | Byers et al. | |
| 4,837,049 A | 6/1989 | Byers et al. | |
| 4,969,468 A | 11/1990 | Byers et al. | |
| 4,991,582 A | 2/1991 | Byers et al. | |
| 5,016,633 A | 5/1991 | Chow | |
| 5,109,844 A | 5/1992 | de Juan, Jr. et al. | |
| 5,215,088 A | 6/1993 | Normann et al. | |
| 5,855,995 A * | 1/1999 | Haq et al. ................... | 428/210 |
| 5,935,155 A | 8/1999 | Humayun et al. | |
| 5,954,751 A * | 9/1999 | Chen et al. .................... | 607/5 |
| 6,256,206 B1 * | 7/2001 | Van Campenhout ........ | 361/760 |
| 6,400,989 B1 | 6/2002 | Eckmiller | |
| 6,458,157 B1 | 10/2002 | Suaning | |
| 7,565,203 B2 * | 7/2009 | Greenberg et al. ............ | 607/54 |

* cited by examiner

*Primary Examiner*—Carl H Layno
*Assistant Examiner*—Brian T Gedeon
(74) *Attorney, Agent, or Firm*—Scott B. Dunbar

(57) ABSTRACT

The present invention is an implantable electronic device formed within a biocompatible hermetic package. Preferably the implantable electronic device is used for a visual prosthesis for the restoration of sight in patients with lost or degraded visual function. The package may include a hard hermetic box, a thin film hermetic coating, or both.

21 Claims, 32 Drawing Sheets

HERMETIC SEALING

COLOR CODING

EXTERNAL/INTERNAL TELEMETRY UNIT –
EXTERNAL COIL/INTERNAL COIL /INTERNAL CHIP

ELECTRODES ON SUBSTRATE

INDIFFERENT ELECTRODE OF MONOPOLAR ELECTRODES

EPIRETINAL ELECTRODES – RECESSED

EPIRETINAL ELECTRODES – PENETRATING

SUBRETINAL ELECTRODES — PENETRATING

ELECTRODES

ELECTRODES

COIL AND WIRE ATTACHMENT TO SUBSTRATES AT ELECTRODE

HERMETIC SEALING

SCANNING SEQUENCE (grid of circled numbers 1 through 200, arranged in 20 rows of 10)

PREDEFINED SEQUENCE  A

FIGURE 17c

ELECTRODE PARAMETERS
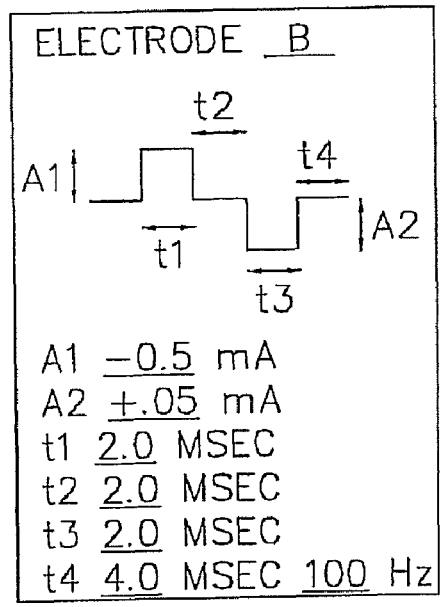
FIGURE 17d
GLOBAL ELECTRODE CONFIGURATION
☐ MONOPOLAR
☐ BIPOLAR
☐ MULTIPOLAR
FIGURE 17e
BIPOLAR
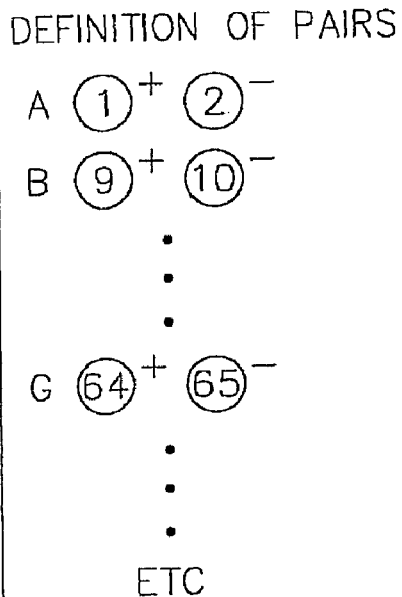
FIGURE 17f
MULTIPOLAR
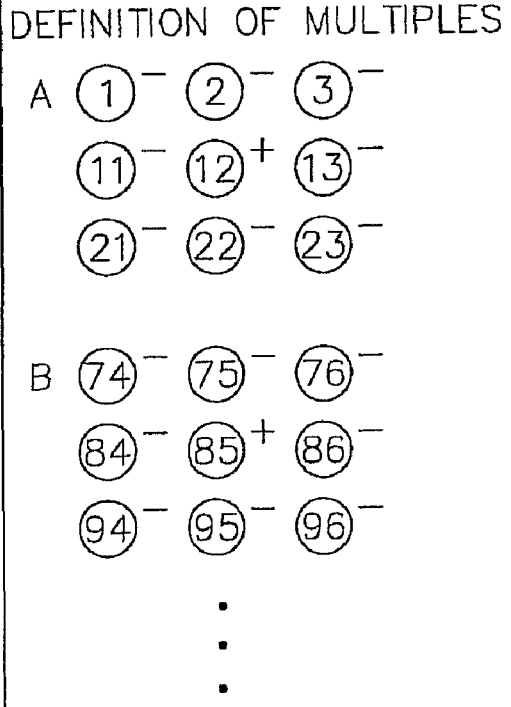
FIGURE 17g

PALM-SIZED TEST UNIT

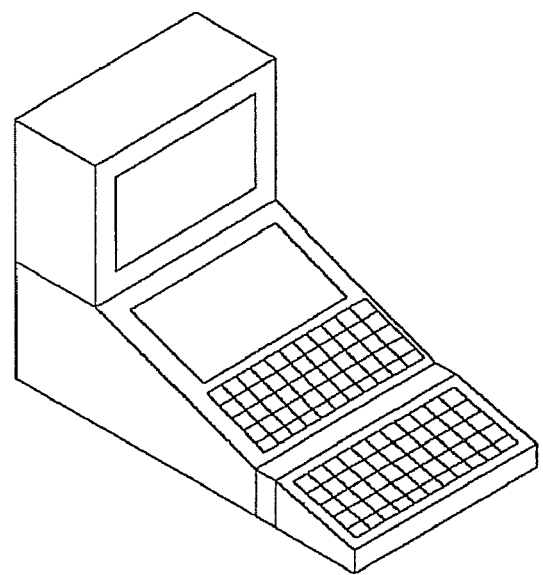
FIGURE 19a
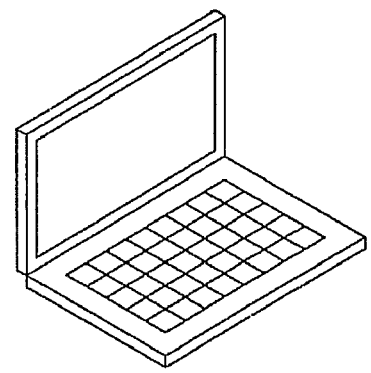
FIGURE 19b
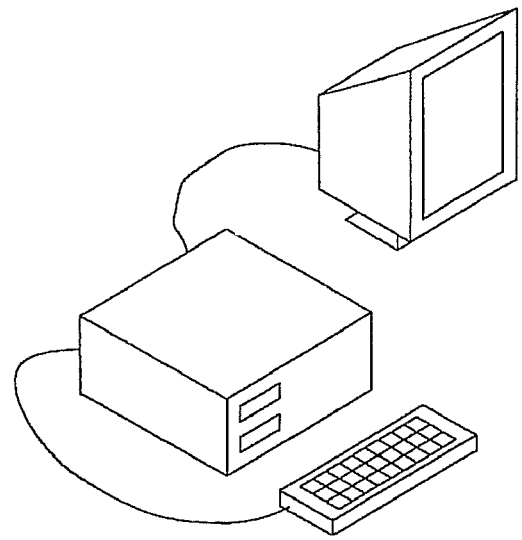

PATIENT CONTROLLER

PACKAGE FOR AN IMPLANTABLE DEVICE

CROSS REFERENCE TO RELATED APPLICATIONS

This application is a Divisional Application of U.S. patent application Ser. No. 11/206,484, filed Aug. 17, 2005, which is a Divisional Application of U.S. patent application Ser. No. 09/515,373, filed Feb. 29, 2000 now abandoned, which claims the benefit of U.S. Provisional Application No. 60/125,873, filed Mar. 24, 1999.

TECHNICAL FIELD OF INVENTION

The present invention relates to electrical stimulation of the retina to produce artificial images for the brain. It relates to electronic image stabilization techniques based on tracking the movements of the eye. It relates to telemetry in and out of the eye for uses such as remote diagnostics and recording from the retinal surface.

The present invention also relates to electrical stimulation of the retina to produce phosphenes and to produce induced color vision. The present invention relates to hermetically sealed electronic and electrode units which are safe to implant in the eye.

BACKGROUND

Color perception is part of the fabric of human experience. Homer (c. 1100 b. c.) writes of "the rosy-fingered dawn". Lady Murasaki no Shikibu (c. 1000 a.d.) uses word colors ("purple, yellow shimmer of dresses, blue paper") in the world's first novel. In the early nineteenth century Thomas Young, an English physician, proposed a trichromatic theory of color vision, based on the action of three different retinal receptors. Fifty years later James Clerk Maxwell, the British physicist and Hermann von Helmholtz, the German physiologist, independently showed that all of the colors we see can be made up from three suitable spectral color lights. In 1964 Edward MacNichol and colleagues at Johns Hopkins and George Wald at Harvard measured the absorption by the visual pigments in cones, which are the color receptor cells. Rods are another type of photoreceptor cell in the primate retina. These cells are more sensitive to dimmer light but are not directly involved in color perception. The individual cones have one of three types of visual pigment. The first is most sensitive to short waves, like blue. The second pigment is most sensitive to middle wavelengths, like green. The third pigment is most sensitive to longer wavelengths, like red.

The retina can be thought of a big flower on a stalk where the top of that stalk is bent over so that the back of the flower faces the sun. In place of the sun think of the external light focused by the lens of the eye onto the back of the flower. The cones and rods cells are on the front of the flower; they get the light which has passed through from the back of the somewhat transparent flower. The photoreceptor nerve cells are connected by synapses to bipolar nerve cells, which are then connected to the ganglion nerve cells. The ganglion nerve cells connect to the optic nerve fibers, which is the "stalk" that carries the information generated in the retina to the brain. Another type of retinal nerve cell, the horizontal cell, facilitates the transfer of information horizontally across bipolar cells. Similarly, another type of cell, the amacrine facilitates the horizontal transfer of information across the ganglion cells. The interactions among the retinal cells can be quite complex. On-center and off-center bipolar cells can be stimulated at the same time by the same cone transmitter release to depolarize and hyperpolarize, respectively. A particular cell's receptive field is that part of the retina, which when stimulated, will result in that cell's stimulation. Thus, most ganglion cells would have a larger receptive field than most bipolar cells. Where the response to the direct light on the center of a ganglion cells receptive field is antagonized by direct light on the surround of its receptive field, the effect is called center-surround antagonism. This phenomenon is important for detecting borders independent of the level of illumination. The existence of this mechanism for sharpening contrast was first suggested by the physicist Ernst Mach in the late 1800's. More detailed theories of color vision incorporate color opponent cells. On the cone level, trichromatic activity of the cone cells occurs. At the bipolar cell level, green-red opponent and blue-yellow opponent processing systems of the center-surround type, occur. For example, a cell with a green responding center would have a annular surround area, which responded in an inhibiting way to red. Similarly there can be red-center responding, green-surround inhibiting response. The other combinations involve blue and yellow in an analogous manner.

It is widely known that Galvani, around 1780, stimulated nerve and muscle response electrically by applying a voltage on a dead frog's nerve. Less well known is that in 1755 LeRoy discharged a Leyden jar, i.e., a capacitor, through the eye of a man who had been blinded by the growth of a cataract. The patient saw "flames passing rapidly downward."

In 1958, Tassicker was issued a patent for a retinal prosthetic utilizing photosensitive material to be implanted sub-retinally. In the case of damage to retinal photoreceptor cells that affected vision, the idea was to electrically stimulate undamaged retinal cells. The photosensitive material would convert the incoming light into an electrical current, which would stimulate nearby undamaged cells. This would result in some kind of replacement of the vision lost. Tassicker reports an actual trial of his device in a human eye. (U.S. Pat. No. 2,760,483).

Subsequently, Michelson (U.S. Pat. No. 4,628,933), Chow (U.S. Pat. Nos. 5,016,633; 5,397,350; 5,556,423), and De Juan (U.S. Pat. No. 5,109,844) all were issued patents relating to a device for stimulating undamaged retinal cells. Chow and Michelson made use of photodiodes and electrodes. The photodiode was excited by incoming photons and produced a current at the electrode.

Normann et al. (U.S. Pat. No. 5,215,088) discloses long electrodes 1000 to 1500 microns long designed to be implanted into the brain cortex. These spire-shaped electrodes were formed of a semiconductor material.

Najafi, et al., (U.S. Pat. No. 5,314,458), disclosed an implantable silicon-substrate based microstimulator with an external device which could send power and signal to the implanted unit by RF means. The incoming RF signal could be decoded and the incoming RF power could be rectified and used to run the electronics.

Difficulties can arise if the photoreceptors, the electronics, and the electrodes all tend to be mounted at one place. One issue is the availability of sufficient area to accommodate all of the devices, and another issue is the amount of power dissipation near the sensitive retinal cells. Since these devices are designed to be implanted into the eye, this potential overheating effect is a serious consideration.

Since these devices are implants in the eye, a serious problem is how to hermetically seal these implanted units. Of further concern is the optimal shape for the electrodes and for the insulators, which surround them. In one embodiment there is a definite need that the retinal device and its electrodes conform to the shape of the retinal curvature and at the same time do not damage the retinal cells or membranes.

The length and structure of electrodes must be suitable for application to the retina, which averages about 200 microns in thickness. Based on this average retinal thickness of 200 microns, elongated electrodes in the range of 100 to 500 microns appear to be suitable. These elongated electrodes reach toward the cells to be activated. Being closer to the targeted cell, they require less current to activate it.

In order not to damage the eye tissue there is a need to maintain an average charge neutrality and to avoid introducing toxic or damaging effects from the prosthesis.

A desirable property of a retinal prosthetic system is making it possible for a physician to make adjustments on an on-going basis from outside the eye. One way of doing this would have a physician's control unit, which would enable the physician to make adjustments and monitor the eye condition. An additional advantageous feature would enable the physician to perform these functions at a remote location, e.g., from his office. This would allow one physician to remotely monitor a number of patients remotely without the necessity of the patient coming to the office. A patient could be traveling distantly and obtain physician monitoring and control of the retinal color prosthetic parameters.

Another version of the physician's control unit is a handheld, palm-size unit. This unit will have some, but not all of the functionality of the physician's control unit. It is for the physician to carry on his rounds at the hospital, for example, to check on post-operative retinal-prosthesis implant patients. Its extreme portability makes other situational uses possible, too, as a practical matter.

The patient will want to control certain aspects of the visual image from the retinal prosthesis system, in particular, image brightness. Consequently, a patient controller, performing fewer functions than the physician's controller is included as part of the retinal prosthetic system. It will control, at a minimum, bright image, and it will control this image brightness in a continuous fashion. The image brightness may be increased or decreased by the patient at any time, under normal circumstances.

A system of these components would itself constitute part of a visual prosthetic to form images in real time within the eye of a person with a damaged retina. In the process of giving back sight to those who are unable to see, it would be advantageous to supply artificial colors in this process of reconstructing sight so that the patient would be able to enjoy a much fuller version of the visual world.

In dealing with externally mounted or externally placed means for capturing image and transmitting it by electronic means or other into the eye, one must deal with the problem of stabilization of the image. For example, a head-mounted camera would not follow the eye movement. It is desirable to track the eye movements relative to the head and use this as a method or approach to solving the image stabilization problem.

By having a method and apparatus for the physician and the technician to initially set up and measure the internal activities and adjust these, the patient's needs can be better accommodated. The opportunity exists to measure internal activity and to allow the physician, using his judgment, to adjust settings and controls on the electrodes. Even the individual electrodes would be adjusted by way of the electronics controlling them. By having this done remotely, by remote means either by telephone or by the Internet or other such, it is clear that a physician would have the capability to intervene and make adjustment as necessary in a convenient and inexpensive fashion, to serve many patients.

SUMMARY OF INVENTION

The objective of the current invention is to restore color vision, in whole or in part, by electrically stimulating undamaged retinal cells, which remain in patients with lost or degraded visual function arising, for example, from Retinitis Pigmentosa or Age-Related Macular Degeneration. This invention is directed toward patients who have been blinded by degeneration of photoreceptors; but who have sufficient bipolar cells, or other cells acting similarly, to permit electrical stimulation.

There are three main functional parts to this invention. One is external to the eye. The second part is internal to the eye. The third part is the communication circuitry for communicating between those two parts. Structurally there are two parts. One part is external to the eye and the other part in implanted within the eye. Each of these structural parts contains two way communication circuitry for communication between the internal and external parts.

The structural external part is composed of a number of subsystems. These subsystems include an external imager, an eye-motion compensation system, a head motion compensation system, a video data processing unit, a patient's controller, a physician's local controller, a physician's remote controller, and a telemetry unit. The imager is a video camera such as a CCD or CMOS video camera. It gathers an image approximating what the eyes would be seeing if they were functional.

The imager sends an image in the form of electrical signals to the video data processing unit. In one aspect, this unit formats a grid-like or pixel-like pattern that is then ultimately sent to electronic circuitry (part of the internal part) within the eye, which drives the electrodes. These electrodes are inside the eye. They replicate the incoming pattern in a useable form for stimulation of the retina so as to reproduce a facsimile of the external scene. In an other aspect of this invention other formats other than a grid-like or pixel like pattern are used, for example a line by line scan in some order, or a random but known order, point-by-point scan. Almost any one-to-one mapping between the acquired image and the electrode array is suitable, as long as the brain interprets the image correctly.

The imager acquires color information. The color data is processed in the video data processing unit. The video data processing unit consists of microprocessor CPU's and associated processing chips including high-speed data signal processing (DSP) chips.

In one aspect, the color information is encoded by time sequences of pulses separated by varying amounts of time; and, the pulse duration may be different for various pulses. The basis for the color encoding is the individual color code reference (FIG. 2a). The electrodes stimulate the target cells so as to create a color image for the patient, corresponding to the original image as seen by the video camera, or other imaging means.

Color information, in an alternative aspect, is sent from the video data processing unit to the electrode array, where each electrode has been determined to stimulate preferentially one of the bipolar cell types, namely, red-center green-surround, green-center-red-surround, blue-center-yellow-surround, or yellow-center-blue-surround.

An eye-motion compensation system is an aspect of this invention. The eye tracker is based on detection of eye motion from the corneal reflex or from implanted coils of wire, or, more generally, insulated conductive coils, on the eye or from the measurement of electrical activity of extra-ocular muscles. Communication is provided between the eye tracker and the video data processing unit by electromagnetic or acoustical telemetry. In one embodiment of the invention, electromagnetic-based telemetry may be used. The results of detecting the eye movement are transmitted to a video data processing unit, together with the information from the camera means. Another aspect of the invention utilizes a head motion sensor and head motion compensation system. The video data processing unit can incorporate the data of the motion of the eye as well as that of the head to further adjust the image electronically so as to account for eye motion and head motion.

The internal structural part which is implanted internally within the eye, is also composed of a number of subsystems. These can be categorized as electronic circuits and electrode arrays, and communication subsystems, which may include electronic circuits. The circuits, the communication subsystems, and the arrays can be hermetically sealed and they can be attached one to the other by insulated wires. The electrode arrays and the electronic circuits can be on one substrate, or they may be on separate substrates joined by an insulated wire or by a plurality of insulated wires. This is similarly the case for a communication subsystem.

A plurality of predominately electronic substrate units and a plurality of predominately electrode units may be implanted or located within the eye as desired or as necessary. The electrodes are designed so that they and the electrode insulation conform to the retinal curvature. The variety of electrode arrays include recessed electrodes so that the electrode array surface coming in contact with the retinal membrane or with the retinal cells is the non-metallic, more inert insulator.

Another aspect of the invention is the elongated electrode, which is designed to stimulate deeper retinal cells by penetrating into the retina by virtue of the length of its electrodes. A plurality of electrodes is used. The elongated electrodes are of lengths from 100 microns to 500 microns. With these lengths, the electrode tips can reach through those retinal cells not of interest but closer to the target stimulation cells, the bipolar cells. The number of electrodes may range from 100 on up to 10,000 or more. With the development of electrode fabrication technology, the number of electrodes might rage up to one million or more.

Another aspect of the invention uses a plurality of capacitive electrodes to stimulate the retina, in place of non-capacitive electrodes. Another aspect of the invention is the use of a neurotrophic factor, for example, Nerve Growth Factor, applied to the electrodes, or to the vicinity of the electrodes, to aid in attracting target nerves and other nerves to grow toward the electrodes.

Hermetic sealing is accomplished by coating the object to be sealed with a substance selected from the group consisting of silicon carbide, diamond-like coating, silicon nitride and silicon oxide in combination, titanium oxide, tantalum oxide, aluminum nitride, aluminum oxide, zirconium oxide. This hermetic sealing aspect of the invention provides an advantageous alternative to glass coverings for hermetic seals, being less likely to become damaged.

Another feature of one aspect of the structural internal-to-the-eye subsystems is that the electronics receive and transmit information in coded or pulse form via electromagnetic waves. In the case where electromagnetic waves are used, the internal-to-the-eye implanted electronics can rectify the RF, or electromagnetic wave, current and decode it. The power being sent in through the receiving coil is extracted and used to drive the electronics. In some instances, the implanted electronics acquire data from the electrode units to transmit out to the video data processing unit.

In another aspect the information coding is done with ultrasonic sound. An ultrasonic transducer replaces the electromagnetic wave receiving coil inside the eye. An ultrasonic transducer replaces the coil outside the eye for the ultrasonic case. By piezoelectric effects, the sound vibration is turned into electrical current, and energy extracted therefrom.

In another aspect of the invention, information is encoded by modulating light. For the light modulation case, a light emitting diode (LED) or laser diode or other light generator, capable of being modulated, acts as the information transmitter. Information is transferred serially by modulating the light beam, and energy is extracted from the light signal after it is converted to electricity. A photo-detector, such as a photodiode, which turns the modulated light signal into a modulated electrical signal, is used as a receiver.

Another aspect of the structural internal-to-the-eye subsystems of this invention is that the predominately electrode array substrate unit and the predominately electronic substrate unit, which are joined by insulated wires, can be placed near each other or in different positions. For example, the electrode array substrate unit can be placed subretinally and the electronic substrate unit placed epiretinally. On a further aspect of this invention, the electronic substrate unit can be placed distant from the retina so as to avoid generating additional heat or decreasing the amount of heat generated near the retinal nerve system. For example, the receiving and processing circuitry could be placed in the vicinity of the pars plana. In the case where the electronics and the electrodes are on the same substrate chip, two of these chips can be placed with the retina between them, one chip subretinal and the other chip epiretinal, such that the electrodes on each may be aligned. Two or more guide pins with corresponding guide hole or holes on the mating chip accomplish the alignment. Alternatively, two or more tiny magnets on each chip, each magnet of the correct corresponding polarity, may similarly align the sub- and epiretinal electrode bearing chips. Alternatively, corresponding parts which mate together on the two different chips and which in a fully mated position hold each other in a locked or "snap-together" relative position.

Now as an element of the external-to-the-eye structural part of the invention, there is a provision for a physician's hand-held test unit and a physician's local or remote office unit or both for control of parameters such as amplitudes, pulse widths, frequencies, and patterns of electrical stimulation.

The physician's hand-held test unit can be used to set up or evaluate and test the implant during or soon after implantation at the patient's bedside. It has, essentially, the capability of receiving what signals come out of the eye and having the ability to send information in to the retinal implant electronic chip. For example, it can adjust the amplitudes on each electrode, one at a time, or in groups. The hand-held unit is primarily used to initially set up and make a determination of the success of the retinal prosthesis.

The physician's local office unit, which may act as a set-up unit as well as a test unit, acts directly through the video data processing unit. The remote physician's office unit would act over the telephone lines directly or through the Internet or a local or wide area network. The office units, local and remote, are essentially the same, with the exception that the physician's remote office unit has the additional communications capability to operate from a location remote from the patient. It may evaluate data being sent out by the internal unit of the eye, and it may send in information. Adjustments to the retinal color prosthesis may be done remotely so that a physician could handle a multiple number of units without leaving his office. Consequently this approach minimizes the costs of initial and subsequent adjustments.

BRIEF DESCRIPTION OF THE DRAWINGS

The above and other features and advantages of the invention will be more apparent from the following detailed description wherein:

FIG. 2b represents an embodiment of the color I conveying method where a "large" electrode stimulates many bipolar cells with the color coding schemata of FIG. 2a;

FIG. 17c represents an electrode scanning sequence, in this case the predefined sequence, A;

FIG. 17d shows electrode parameters, here for electrode B, including current amplitudes and waveform timelines;

FIG. 17e illustrates the screen for choosing the global electrode configuration, monopolar, bipolar, or multipolar;

FIG. 17f renders a screen showing the definition of bipolar pairs (of electrodes);

FIG. 17g shows the definition of the multipole arrangements;

FIG. 19a-c show the physician's remote controller that has the same functionality inside as the physician's controller but with the addition of communication means such as telemetry or telephone modem.

DESCRIPTION OF THE PREFERRED EMBODIMENTS

The following description is of the best mode presently contemplated for carrying out the invention. This description is not to be taken in a limiting sense, but is merely made for the purpose of describing the general principles of the invention. The scope of the invention should be determined with reference to the claims.

Objective

The objective of the embodiments of the current invention is a retinal color prosthesis to restore color vision, in whole or in part, by electrically stimulating undamaged retinal cells, which remain in patients with, lost or degraded visual function. Embodiments of this retinal color prosthesis invention are directed toward helping patients who have been blinded by degeneration of photoreceptors and other cells; but who have sufficient bipolar cells and the like to permit the perception of color vision by electric stimulation. By color vision, it is meant to include black, gray, and white among the term color.

General Description

Figure 1A:
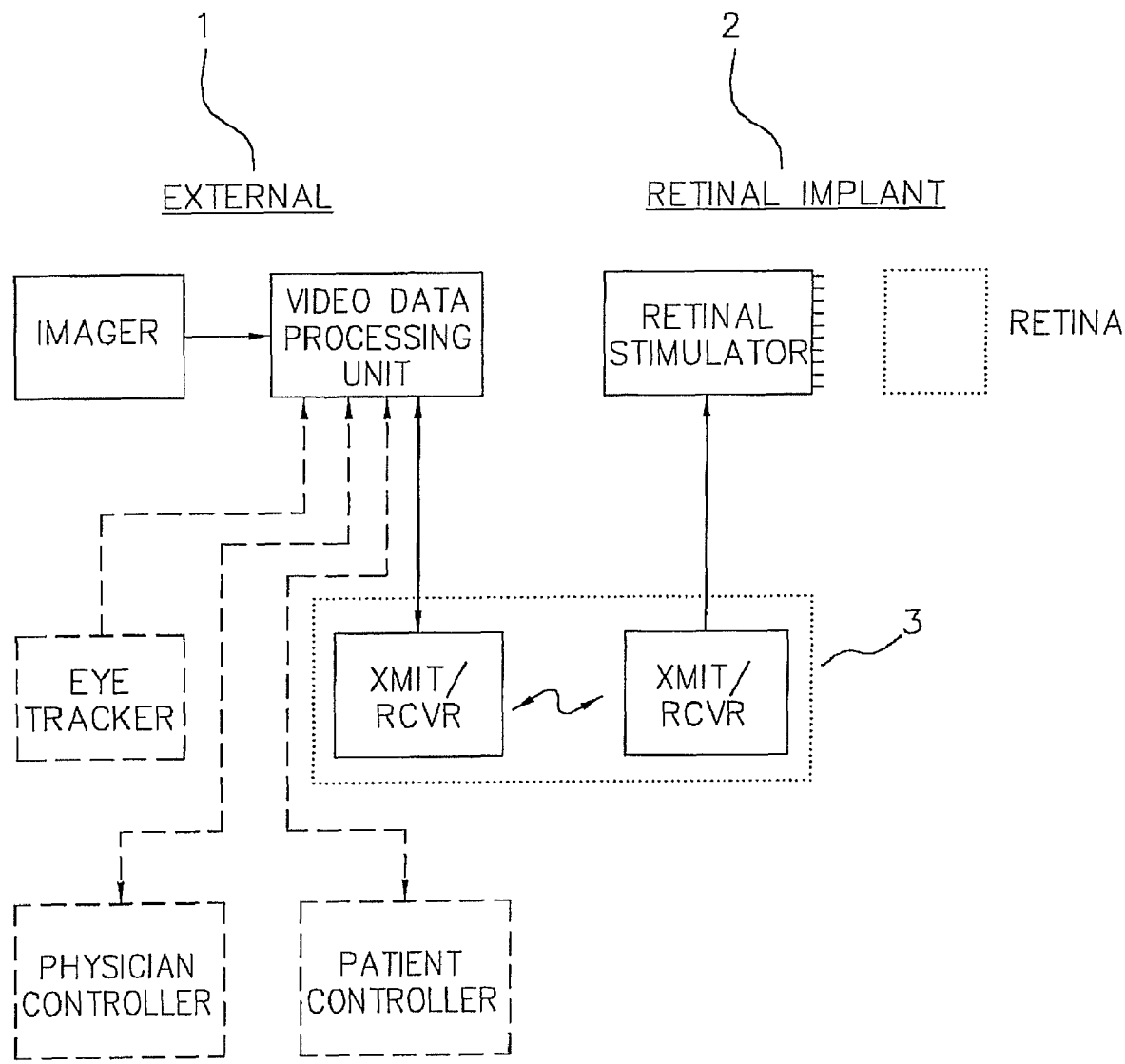
FIG. 1a shows the general structural aspects of the retina color prosthesis system.

Functionally, there are three main parts to an embodiment of this retinal color prosthesis invention. See FIG. 1a. FIG. 1a is oriented toward showing the main structural parts and subsystems, with a dotted enclosure to indicate a functional intercommunications aspect. The first part of the embodiment is external (1) to the eye. The second part is implanted internal (2) to the eye. The third part is means for communication between those two parts (3). Structurally there are two parts. One part is external (1) to the eye and the other part (2) is implanted within the eye. Each of these structural parts contains two way communication circuitry for communication (3) between the internal (2) and external (1) parts.

The external part of the retinal color prosthesis is carried by the patient. Typically, the external part including imager, video data processing unit, eye-tracker, and transmitter/receiver are worn as an eyeglass-like unit. Typical of this embodiment, a front view of one aspect of the structural external part (1) of the color retinal prosthesis is shown in FIG. 1c and a side view is shown in FIG. 1d, (1). In addition, there are two other units which may be plugged into the external unit; when this is done they act as part of the external unit. The physician's control unit is not normally plugged into the external part worn by the patient, except when the physician is conducting an examination and adjustment of the retinal color prosthetic. The patient's controller may or may not be normally plugged in. When the patient's controller is plugged in, it can also receive signals from a remote physician's controller which then acts in the same way as the plug-in physician's controller.

Figure 1B:
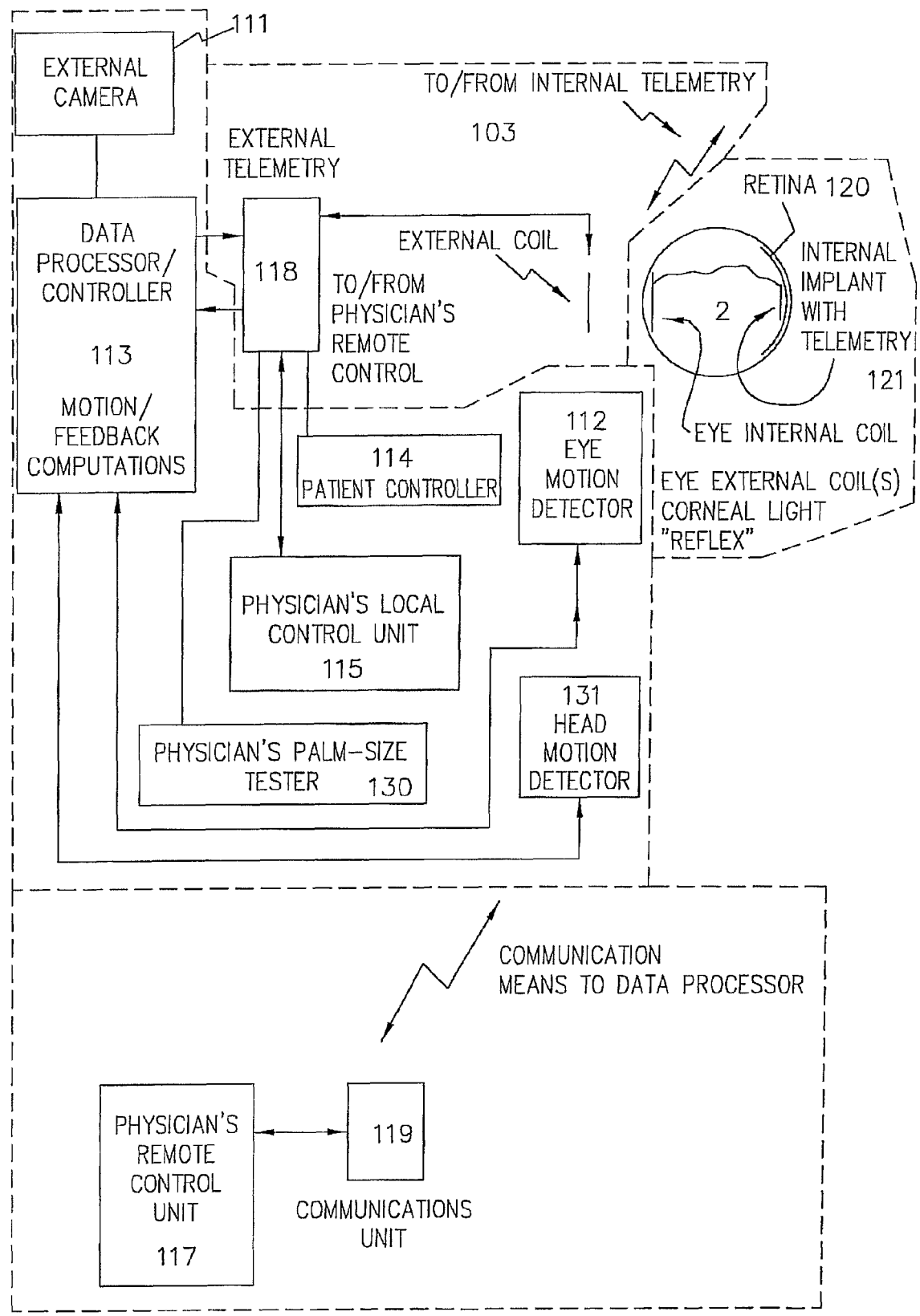
FIG. 1b shows the retina color prosthesis system with a structural part internal (to the eye), with an external part with subsystems for eye-motion feedback to enable maintaining a stable image presentation, and with a subsystems for communicating between the internal and external parts, and other structural subsystems.
Figure 1C:
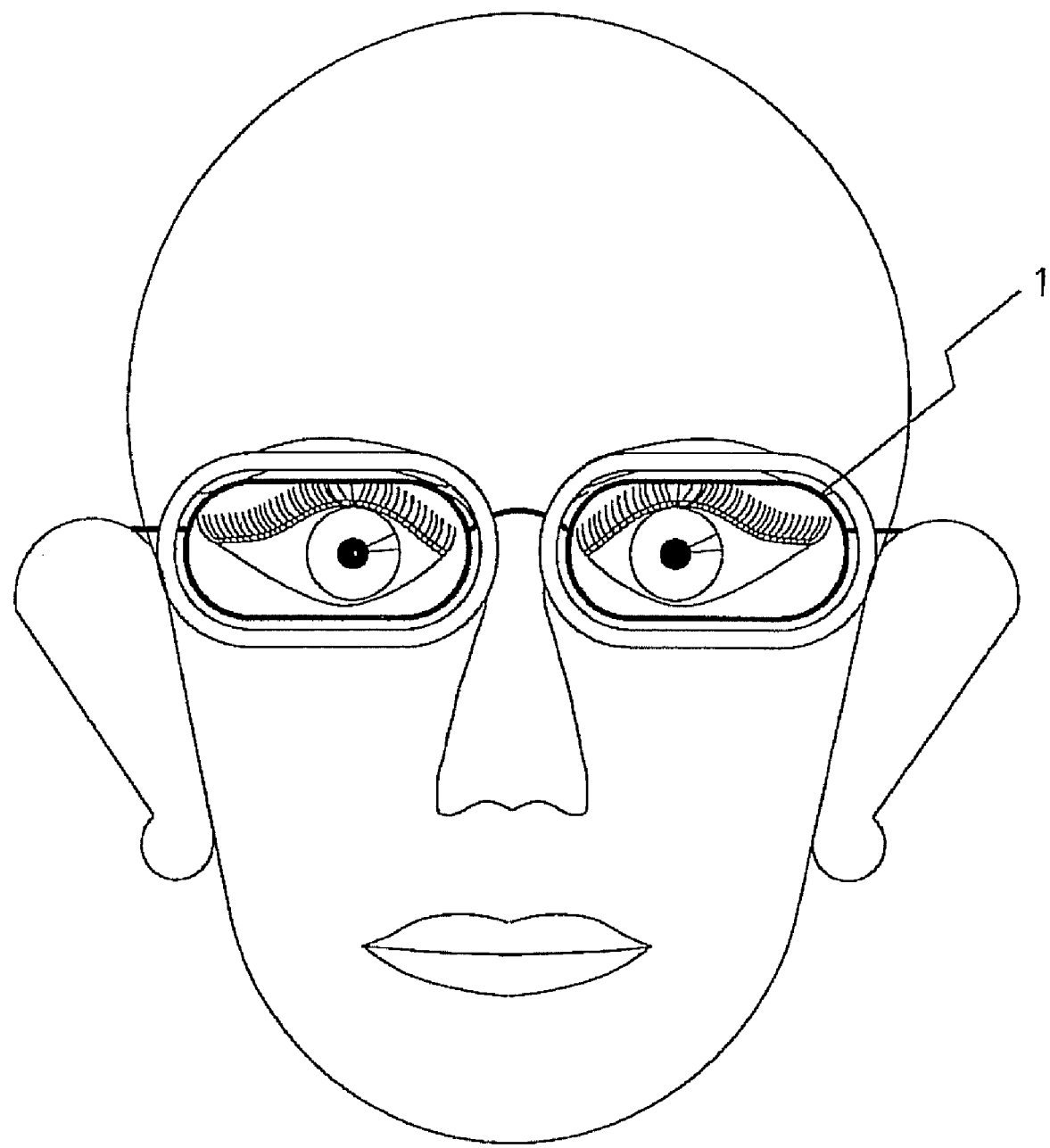
FIG. 1c shows an embodiment of the retina color prosthesis system which is, in part, worn in eyeglass fashion.
Figure 1D:
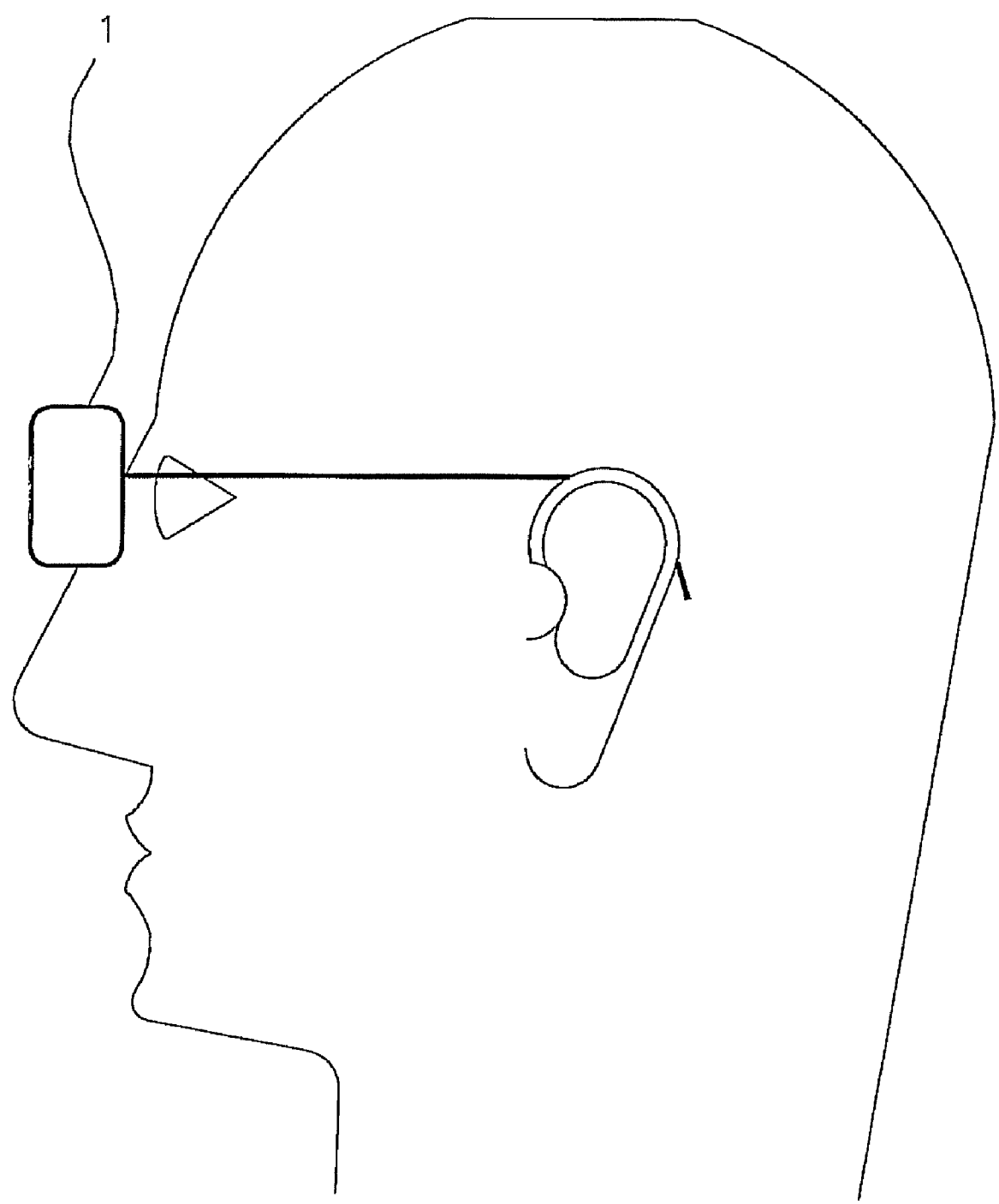
FIG. 1d shows the system in FIG. 1c in side view.

Examining further the embodiment of the subsystems of the external part, see FIG. 1b. These include an external color imager (111), an eye-motion compensation system (112), a head-motion compensation system (131), a processing unit (113), a patient's controller (114), a physician's local controller (115), a physicians hand-held palm-size pocket-size unit (130), a physician's remote controller (117), and a telemetry means (118). The color imager is a color video camera such as a CCD or CMOS video camera. It gathers an image approximating what the eyes would be seeing if they were functional.

An external imager (111) sends an image in the form of electrical signals to the video data processing unit (113). The video data processing unit consists of microprocessor CPU's and associated processing chips including high-speed data signal processing (DSP) chips. This unit can format a grid-like or pixel-like pattern that is sent to the electrodes by way of the telemetry communication subsystems (118, 121). See FIG. 1b. In this embodiment of the retinal color prosthesis (FIG. 1b, (121)), these electrodes are incorporated in the internal-to-the eye implanted part.

These electrodes, which are part of the internal implant (121), together with the telemetry circuitry (121) are inside the eye. With other internally implanted electronic circuitry (121), they cooperate with the electrodes so as to replicate the incoming pattern, in a useable form, for stimulation of the retina so as to reproduce a facsimile perception of the external scene. The eye-motion (112) and head-motion (131) detectors supply information to the video data processing unit (113) to shift the image presented to the retina (120).

There are three preferred embodiments for stimulating the retina via the electrodes to convey the perception of color. Color information is acquired by the imaging means (111). The color data is processed in the video data processing unit (113).

First Preferred Color Mode

Figure 2A:
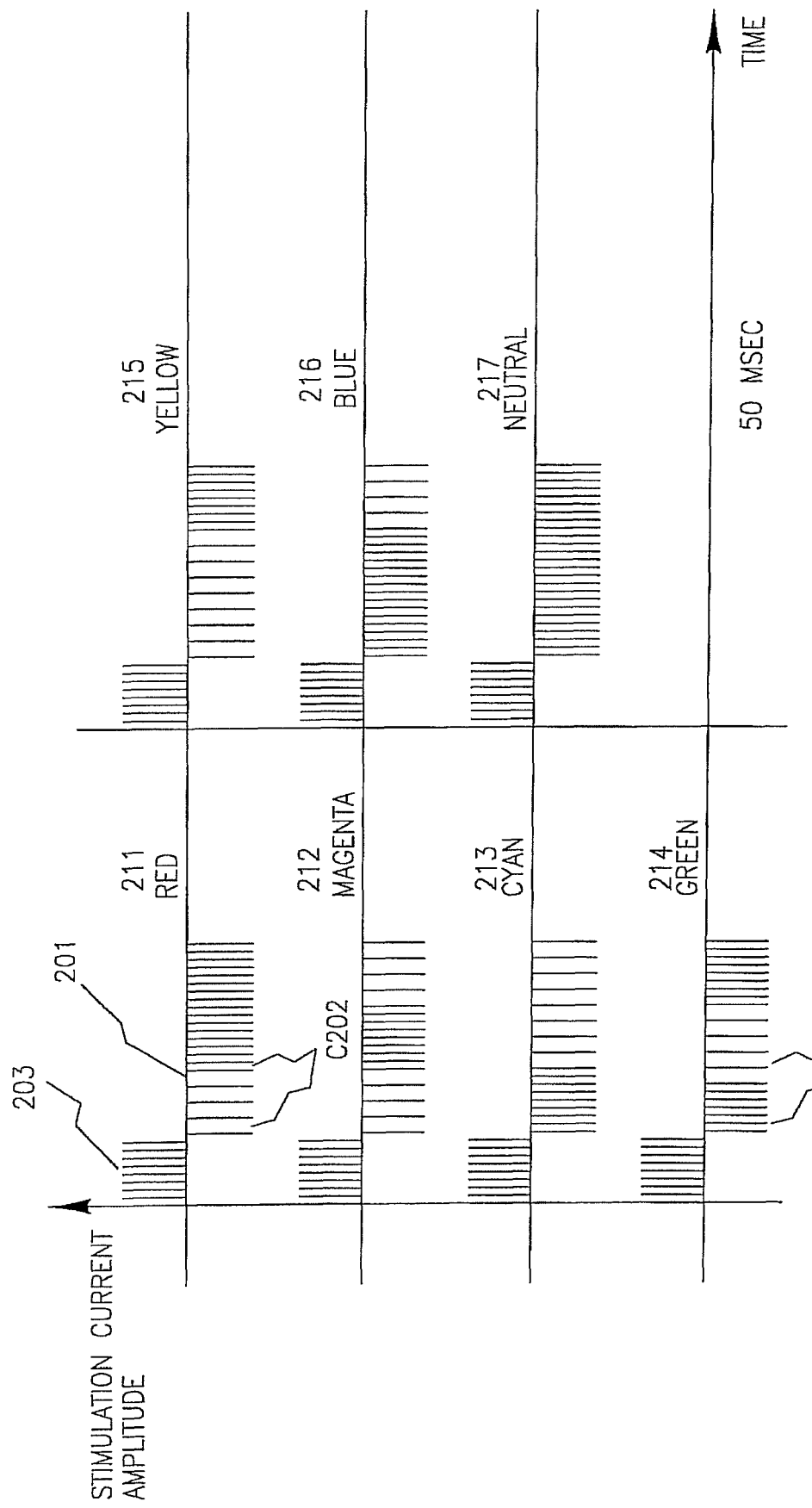
FIG. 2a shows an embodiment of the color I coding schemata for the stimulation of the sensation of color.
Figure 2B:
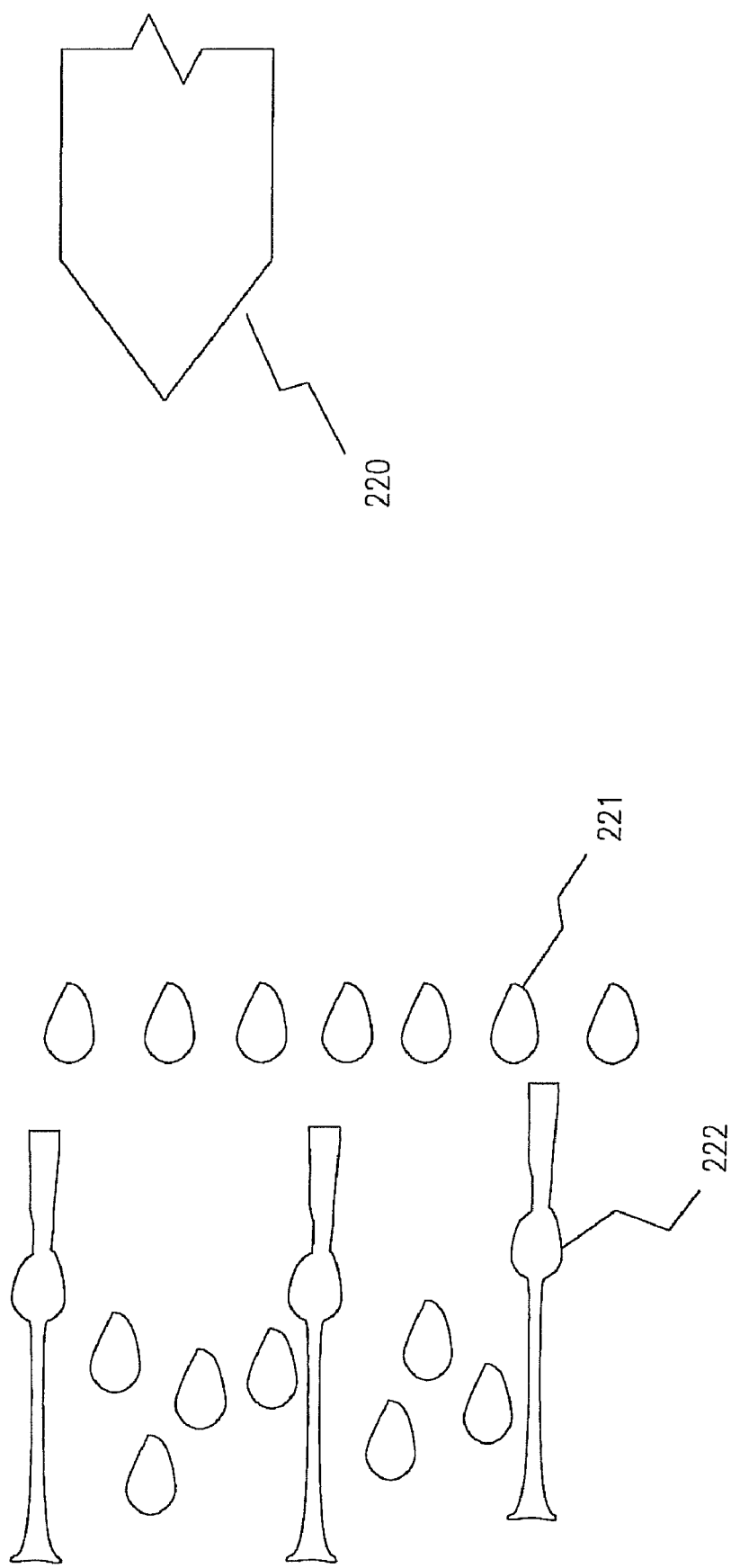
Figure 2C:
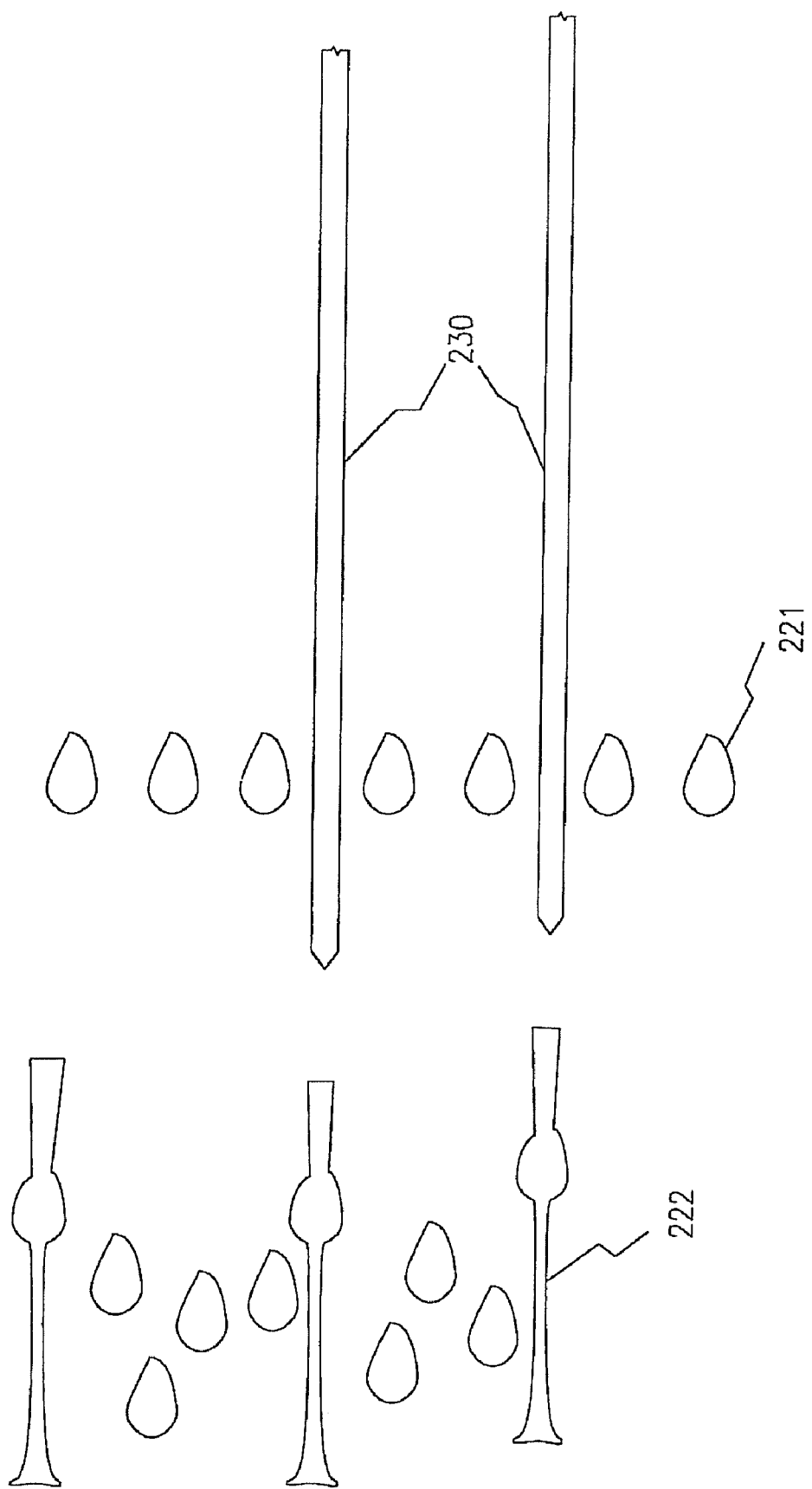
FIG. 2c represents an embodiment of the color II conveying method where an individual electrode stimulates a single type of bipolar cell.

Color information (See FIG. 2a), in the first preferred embodiment, is encoded by time sequences of pulses (201) separated by varying amounts of time (202), and also with the pulse duration being varied in time (203). The basis for the color encoding is the individual color code reference (211 through 217). The electrodes stimulate the target cells so as to create a color image for the patient, corresponding to the original image as seen by the video camera, or other imaging means. Using temporal coding of electrical stimuli placed (cf. FIG. 2b, 220, FIG. 2c, 230) on or near the retina (FIG. 2b and FIG. 2c, 221, 222) the perception of color can be created in patients blinded by outer retinal degeneration. By sending different temporal coding schemes to different electrodes, an image composed of more than one color can be produced. FIG. 2 shows one stimulation protocol. Cathodic stimuli (202) are below the zero plane (220) and anodic stimuli (203) are above. All the stimulus rates are either "fast" (203) or "slow" (202) except for green (214), which includes an intermediate stimulus rate (204). The temporal codes for the other colors are shown as Red (211), as Magenta (212), as Cyan (213), as Yellow (215), as Blue (216), as Neutral (217). This preferred embodiment is directed toward electrodes which are less densely packed in proximity to the retinal cells.

Second Preferred Color Mode

Color information, in a second preferred embodiment, is sent from the video data processing unit to the electrode array, where each electrode has been determined by test to stimulate one of a bipolar type: red-center green-surround, green-center-red-surround, blue-center-yellow-surround, or yellow-center-blue-surround. In this embodiment, electrodes which are small enough to interact with a single cell, or at most, a few cells are placed in the vicinity of individual bipolar cells, which react to a stimulus with nerve pulse rates and nerve pulse structure (i.e., pulse duration and pulse amplitude). Some of the bipolar cells, when electrically, or otherwise, stimulated, will send red-green signals to the brain. Others will send yellow-blue signals. This refers to the operation of the normal retina. In the normal retina, red or green color photoreceptors (cone cells) send nerve pulses to the red-green bipolar cell which then pass some form of this information up to the ganglion cells and then up to the visual cortex of the brain. With small electrodes individual bipolar cells can be excited in a spatial, or planar, pattern. Small electrodes are those with tip from 0.1 μm to 15 μm, and which individual electrodes are spaced apart from a range 8 μm to 24 μm, so as to approximate a one-to-one correspondence with the bipolar cells. The second preferred embodiment is oriented toward a more densely packed set of electrodes.

Third Preferred Color Mode

A third preferred mode is a combination of the first and of the second preferred modes such that a broader area coverage of the color information encoded by time sequences of pulses, of varying widths and separations and with relatively fewer electrodes is combined with a higher density of electrodes, addressing more the individual bipolar cells.

First Order and Higher Effects

Regardless of a particular theory of color vision, the impinging of colored light on the normal cones, and possibly rods, give rise in some fashion to the perception of color, i.e., multi-spectral vision. In the time-pulse coding color method, above, the absence of all, or sufficient, numbers of working cones (and rods) suggests a generalization of the particular time-pulse color encoding method. The generalization is based on the known, or partly known, neuron conduction pathways in the retina. The cone cells, for example, signal to bipolar cells, which in turn signal the ganglion cells. The original spatial-temporal-color (including black, white) scheme for conveying color information as the cone is struck by particular wavelength photons is then transformed to a patterned signal firing of the next cellular level, say the bipolar cells, unless the cones are absent or don't function. Thus, this second level of patterned signal firing is what one wishes to supply to induce the perception of color vision.

The secondary layer of patterned firing may be close to the necessary primary pattern, in which case the secondary pattern (S) may be represented as $P*(1+\epsilon)$. The * indicates matrix multiplication. P is the primary pattern, represented as a matrix P=

$$\begin{bmatrix} p_{11} & p_{1j} \\ p_{k1} & p_{kj} \end{bmatrix}$$

where P represents the light signals of a particular spatial-temporal pattern, e.g., flicker signals for green. The output from the first cell layer, say the cones, is then S, the secondary pattern. This represents the output from the bipolar layer in response to the input from the first (cone) layer. If $S=P*(1+\epsilon)$, where 1 represents a vector and $\epsilon$ represents a small deviation applied to the vector 1, then S is represented by P to the lowest order, and by $P*(1+\epsilon)$ to the next order. Thus, the response may be seen as a zero order effect and a first order linear effect. Additional terms in the functional relationship are included to completely define the functional relationship. If S is some non-linear function of P, finding S by starting with P requires more terms then the linear case to define the bulk of the functional relationship. However, regardless of the details of one color vision theory or another, on physiological grounds S is some function of P. As in the case of fitting individual patients with lenses for their glasses, variations of parameters are expected in fitting each patient to a particular temporal coding of electrical stimuli.

Scaling Data from Photoreceptors to Bipolar Cells

As cited above, Greenberg (1998), indicates that electrical and photic stimulation of the normal retina operate via similar mechanisms. Thus, even though electrical stimulation of a retina damaged by outer retinal degeneration is different from the electrical stimulation of a normal retina, the temporal relationships are expected to be analogous.

To explain this, it is noted that electrical stimulation of the normal retinal is accomplished by stimulating the photoreceptor cells (including the color cells activated differentially according to the color of light impinging on them). For the outer retinal degeneration, it is precisely these photoreceptor cells which are missing. Therefore, the electrical stimulation in this case proceeds by way of the cells next up the ladder toward the optic nerve, namely, the bipolar cells.

The time constant for stimulating photoreceptor is about 20 milliseconds. Thus the electrical pulse duration would need to be at least 20 milliseconds. The time constant for stimulating bipolar cells is around 9 seconds. These time constants are much longer than for the ganglion cells (about 1 millisecond). The ganglion cells are another layer of retinal cells closer to the optic nerve. The actual details of the behavior of the different cell types of the retina are quite complicated including the different relationships for current threshold versus stimulus duration (cf. Greenberg, 1998). One may, however, summarize an apparent resonant response of the cells based on their time constants corresponding to the actual pulse stimulus duration.

In FIG. 2, which is extrapolated from external-to-the-eye electrical stimulation data of Young (1977) and from light stimulation data of Festinger, Allyn, and White (1971), there is shown data that would be applicable to the photoreceptor cells. One may scale the data down based on the ratio of the photoreceptor time constant (about 20 milliseconds) to that of the bipolar cells (about 9 milliseconds). Consequently, 50 milliseconds on the time scale in FIG. 2 now corresponds to 25 milliseconds. Advantageously, stimulation rates and duration of pulses, as well as pulse widths may be chosen which apply to the electrode stimulation of the bipolar cells of the retina.

Eye Movement/Head Motion Compensation

In a preferred embodiment, an external imager such as a color CCD or color CMOS video camera (111) and a video data processing unit (113), with an external telemetry unit (118) present data to the internal eye-implant part. Another aspect of the preferred embodiment is a method and apparatus for tracking eye movement (112) and using that information to shift (113) the image presented to the retina. Another aspect of the preferred embodiment utilizes a head motion sensor (131) and a head motion compensation system (131, 113). The video data processing unit incorporates the data of the motion of the eye as well as that of the head to further adjust the image electronically so as to account for eye motion and head motion. Thus electronic image compensation, stabilization and adjustment are provided by the eye and head movement compensation subsystems of the external part of the retinal color prosthesis.

Logarithmic Encoding of Light

In one aspect of an embodiment (FIG. 1b), light amplitude is recorded by the external imager (111). The video data processing unit uses a logarithmic encoding scheme (113) to convert the incoming light amplitudes into the logarithmic electrical signals of these amplitudes (113). These electrical signals are then passed on by telemetry (118), (121), to the internal implant (121) which results in the retinal cells (120) being stimulated via the implanted electrodes (121), in this embodiment as part of the internal implant (121). Encoding is done outside the eye, but may be done internal to the eye, with a sufficient internal computational capability.

Energy and Signal Transmission

Coils

Figure 3A:
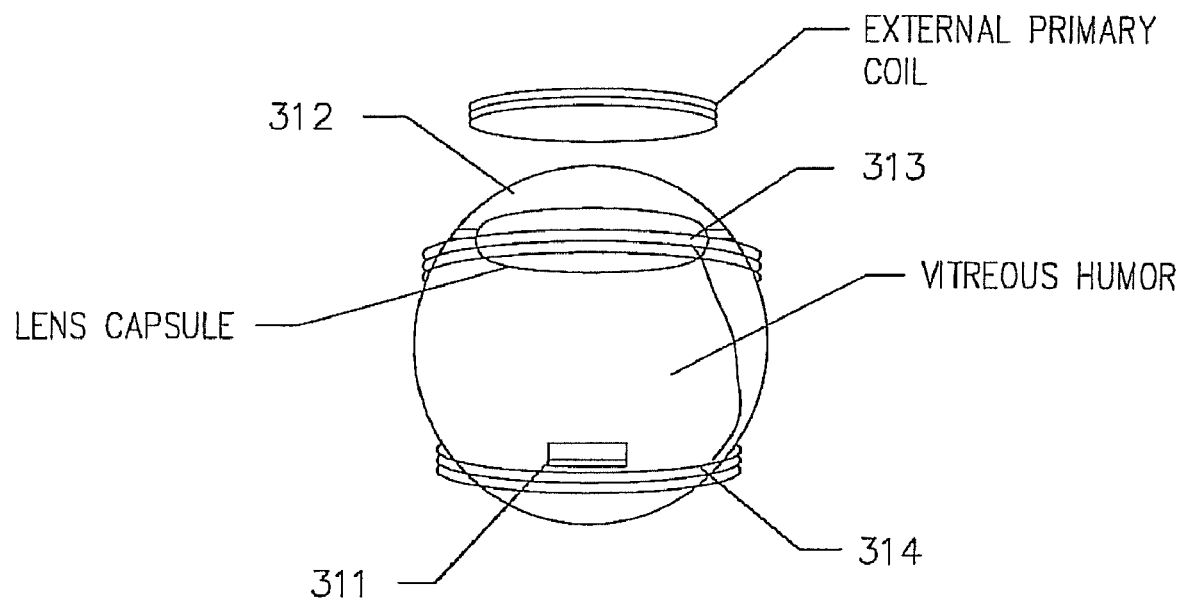
FIG. 3a represents an embodiment of the telemetry unit including an external coil, an internal (to the eye) coil, and an internal electronic chip.
Figure 3B:
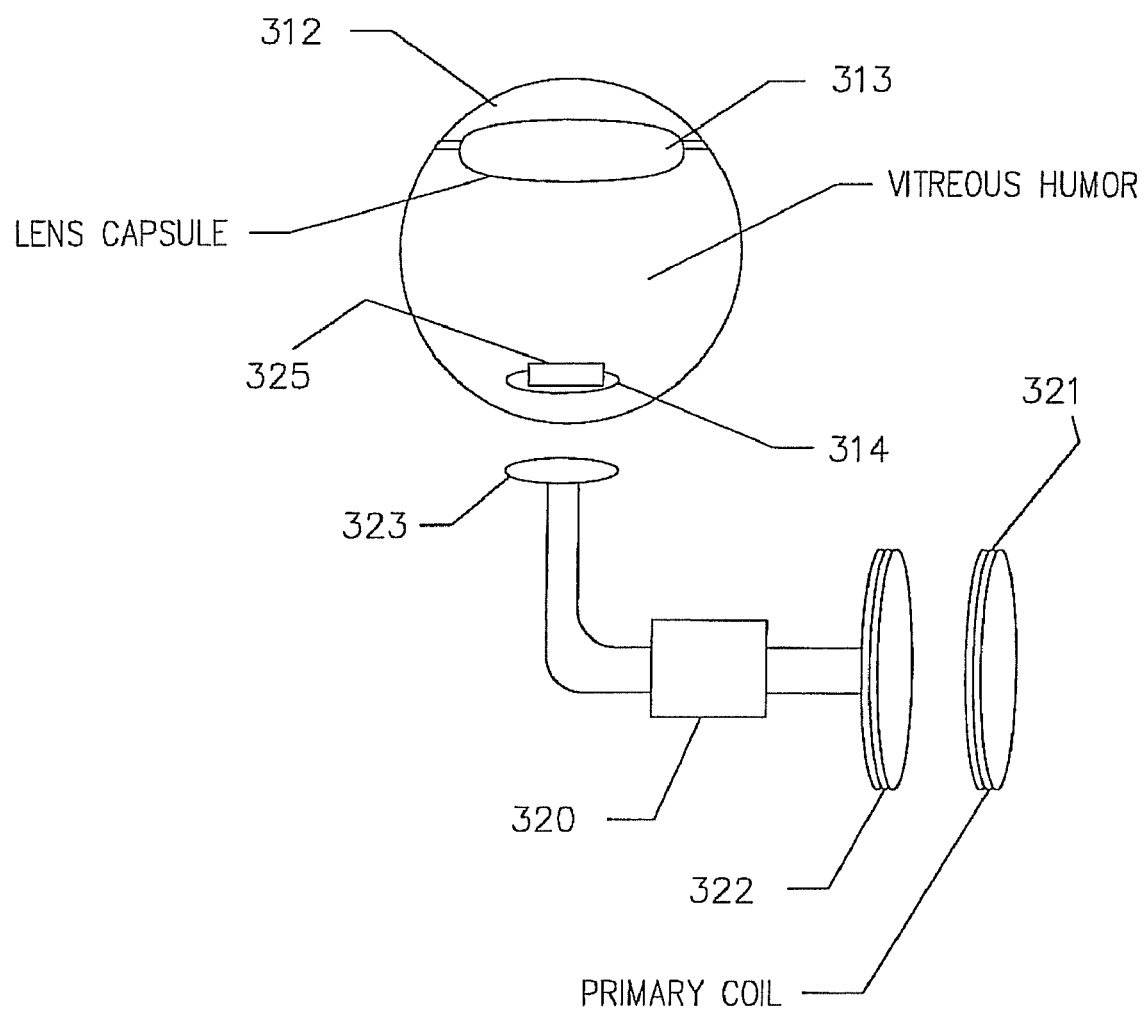
FIG. 3b represents an embodiment of the telemetry unit including an external coil, an internal (to the eye) coil, an external electronic chip, a dual coil transfer unit, and an internal electrode array.

The retinal prosthesis system contains a color imager (FIG. 1b, 111) such as a color CCD or CMOS video camera. The imaging output data is typically processed (113) into a pixel-based format compatible with the resolution of the implanted system. This processed data (113) is then associated with corresponding electrodes and amplitude and pulse-width and frequency information is sent by telemetry (118) into the internal unit coils, (311), (313), (314) (see FIG. 3a). Electromagnetic energy, is transferred into and out from an electronic component (311) located internally in the eye (312), using two insulated coils, both located under the conjunctiva of the eye with one free end of one coil (313) joined to one free end of the second coil (314), the second free end of said one coil joined to the second free end of said second coil. The second coil (314) is located in proximity to a coil (311) which is a part of said internally located electronic component, or, directly to said internally located electronic component (311). The larger coil is positioned near the lens of the eye. The larger coil is fastened in place in its position near the lens of the eye, for example, by suturing. FIG. 3b represents an embodiment of the telemetry unit temporally located near the eye, including an external temporal coil (321), an internal (to the eye) coil (314), an external-to-the-eye electronic chip (320), dual coil transfer units (314, 323), (321,322) and an internal-to-the-eye electrode array (325). The advantage of locating the external electronics in the fatty tissue behind the eye is that there is a reasonable amount of space there for the electronics and in that position it appears not to interfere with the motion of the eye.

Ultrasonic Sound

Figure 3C:
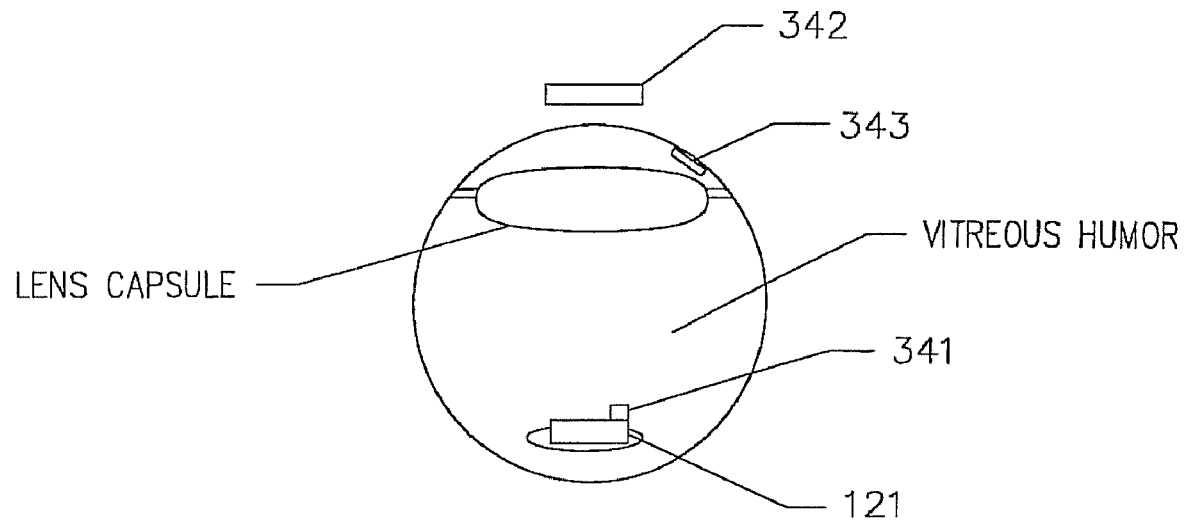
FIG. 3c shows and acoustic energy and information transfer system.

In another aspect the information coding is done with ultrasonic sound and in a third aspect information is encoded by modulating light. An (FIG. 3c) ultrasonic transducer (341) replaces the electromagnetic wave receiving coil on the implant (121) inside the eye. An ultrasonic transducer (342) replaces the coil outside the eye for the ultrasonic case. A transponder (343) under the conjunctiva of the eye may be used to amplify the acoustic signal and energy either direction. By piezoelectric effects, the sound vibration is turned into electrical current, and energy extracted therefrom.

Modulated Light Beam

Figure 3D:
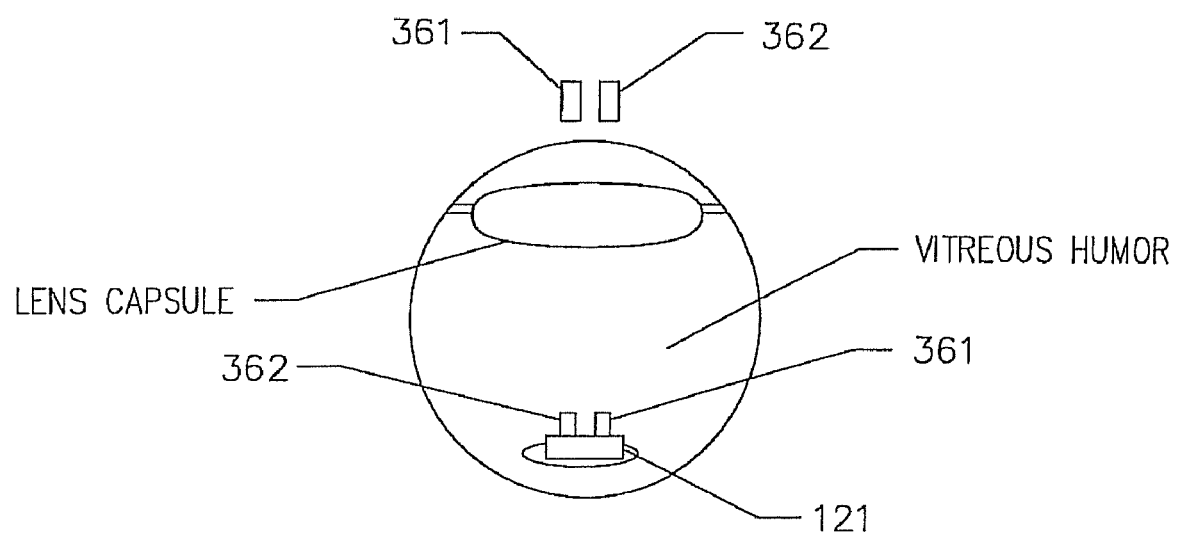
FIG. 3d shows a light energy and information transfer system.
Figure 5:
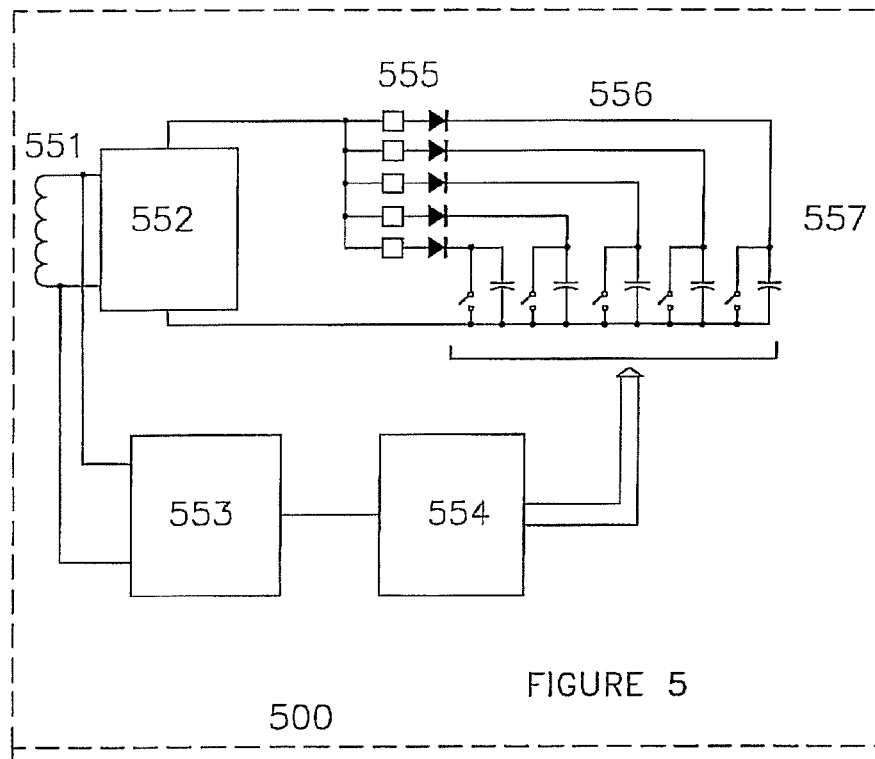
FIG. 5 shows an embodiment of an internal telemetry circuit and electrode array switcher.
Figure 4:
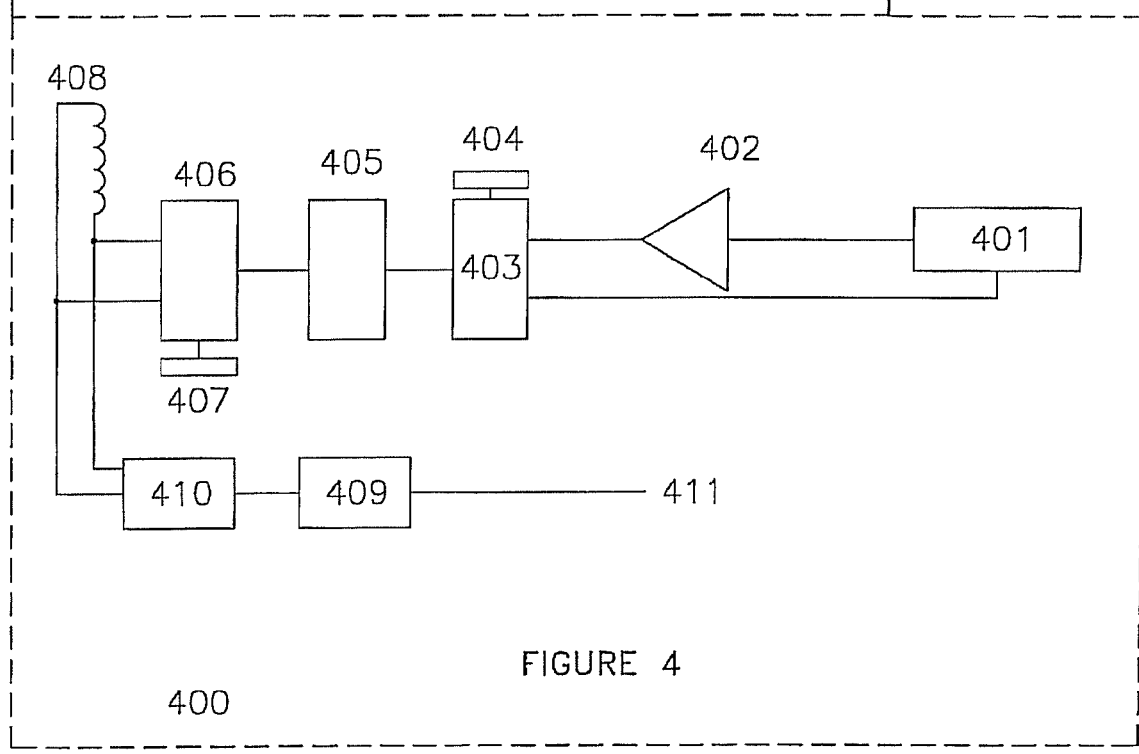
FIG. 4 represents an embodiment of the external telemetry unit.

For the light modulation (FIG. 3d) case, a light emitting diode (LED) or laser diode or other light generator (361), capable of being modulated, acts as the information transmitter. Information is transferred serially by modulating the light beam, and energy is extracted from the light signal after it is converted to electricity. A photo-detector (362), such as a photodiode, which turns the modulated light signal into a modulated electrical signal, is used as a receiver. A set of a photo-generator and a photo-detector are on the implant (121) and a set is also external to the eye Prototype-like Device FIG. 4 shows an example of the internal-to-the-eye and the external-to-the eye parts of the retinal color prosthesis, together with a means for communicating between the two. The video camera (401) connects to an amplifier (402) and to a microprocessor (403) with memory (404). The microprocessor is connected to a modulator (405). The modulator is connected to a coil drive circuit (406). The coil drive circuit is connected to an oscillator (407) and to the coil (408). The coil (408) can receive energy inductively, which can be used to recharge a battery (410), which then supplies power. The battery may also be recharged from a charger (409) on a power line source (411).

The internal-to-the eye implanted part shows a coil (551), which connects to both a rectifier circuit (552) and to a demodulator circuit (553). The demodulator connects to a switch control unit (554). The rectifier (552) connects to a plurality of diodes (555) which rectify the current to direct current for the electrodes (556); the switch control sets the electrodes as on or off as they set the switches (557). The coils (408) and (551) serve to connect inductively the internal-to-the-eye (500) subsystem and the external-to-the patient (400) subsystem by electromagnetic waves. Both power and information can be sent into the internal unit. Information can be sent out to the external unit. Power is extracted from the incoming electromagnetic signal and may be accumulated by capacitors connected to each electrode or by capacitive electrodes themselves.

Simple Electrode Implant

Figure 6A:
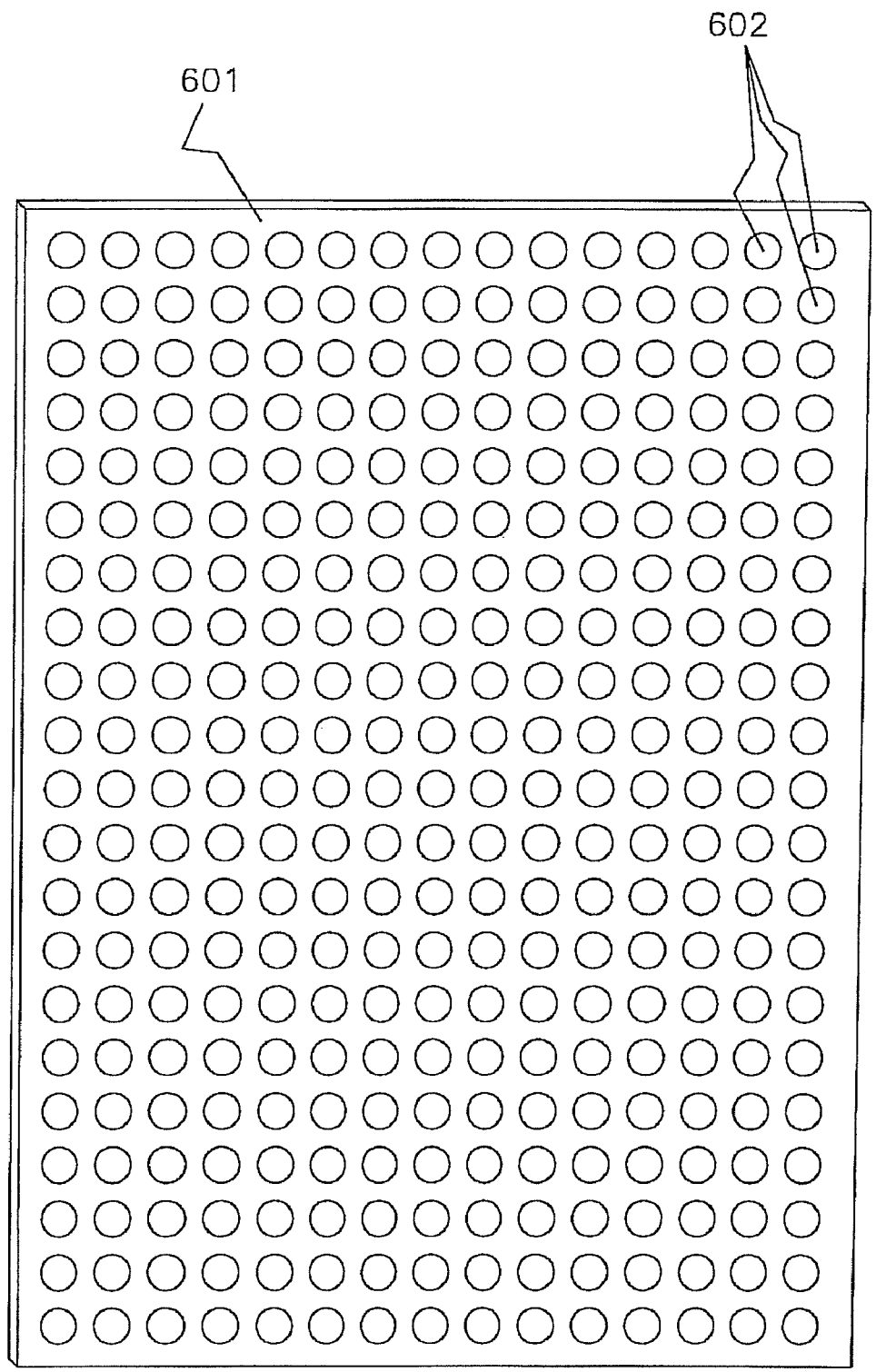
FIG. 6a shows a monopolar electrode arrangement and illustrates a set of round electrodes on a substrate material.
Figure 6B:
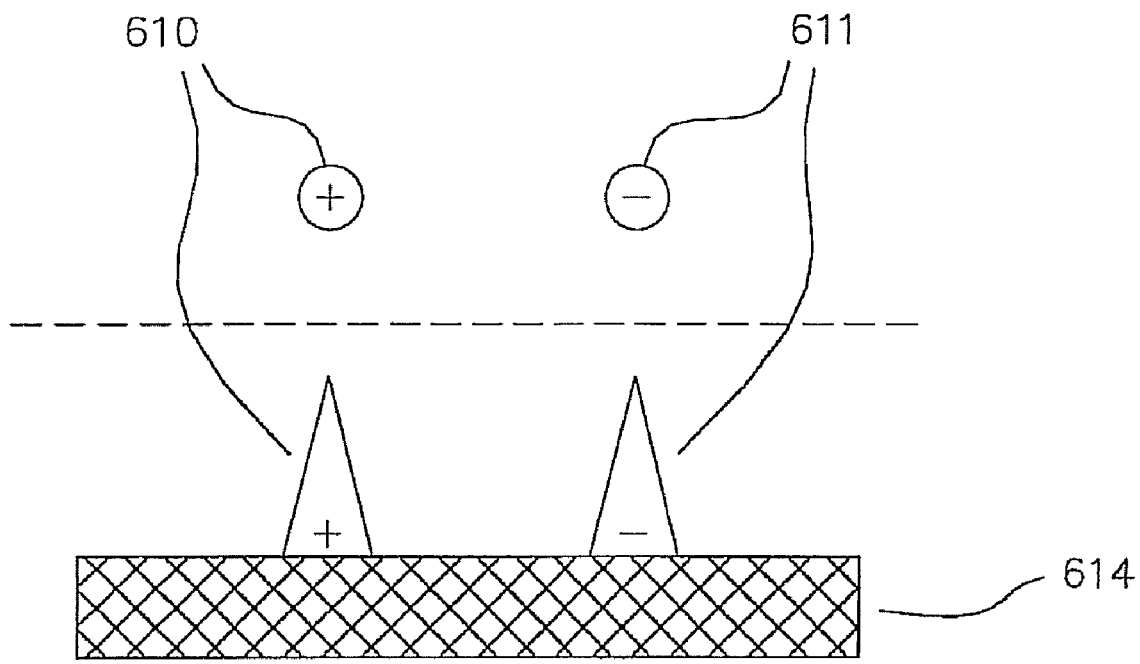
FIG. 6b shows a bipolar electrode arrangement.
Figure 6C:
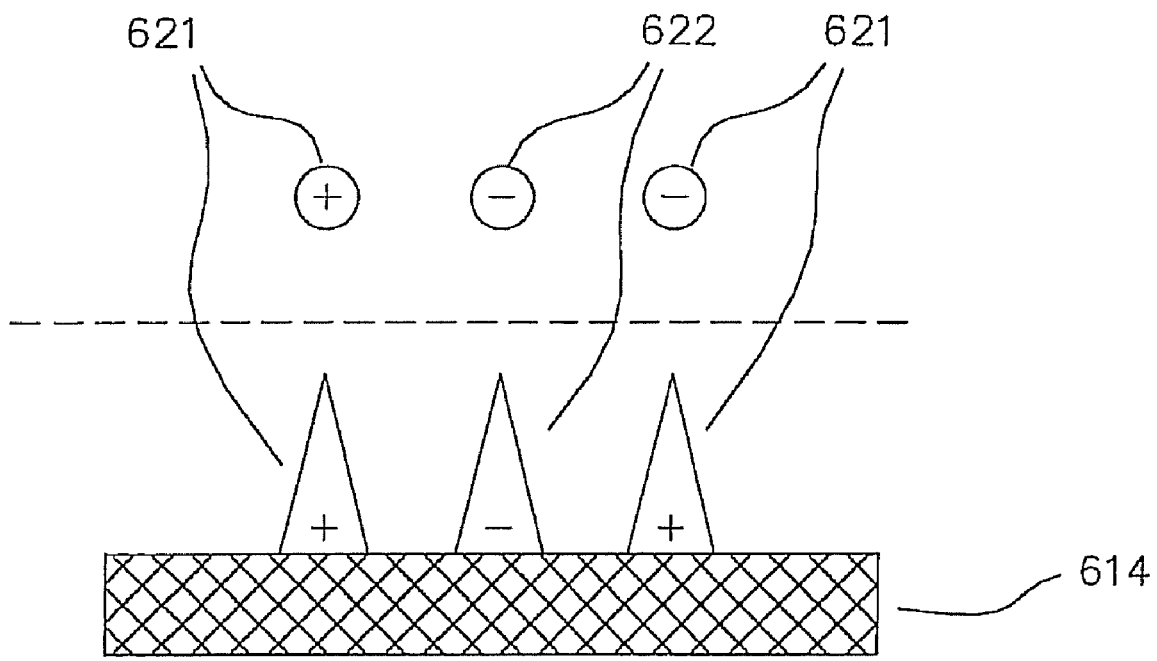
FIG. 6c shows a multipolar electrode arrangement.
Figure 7:
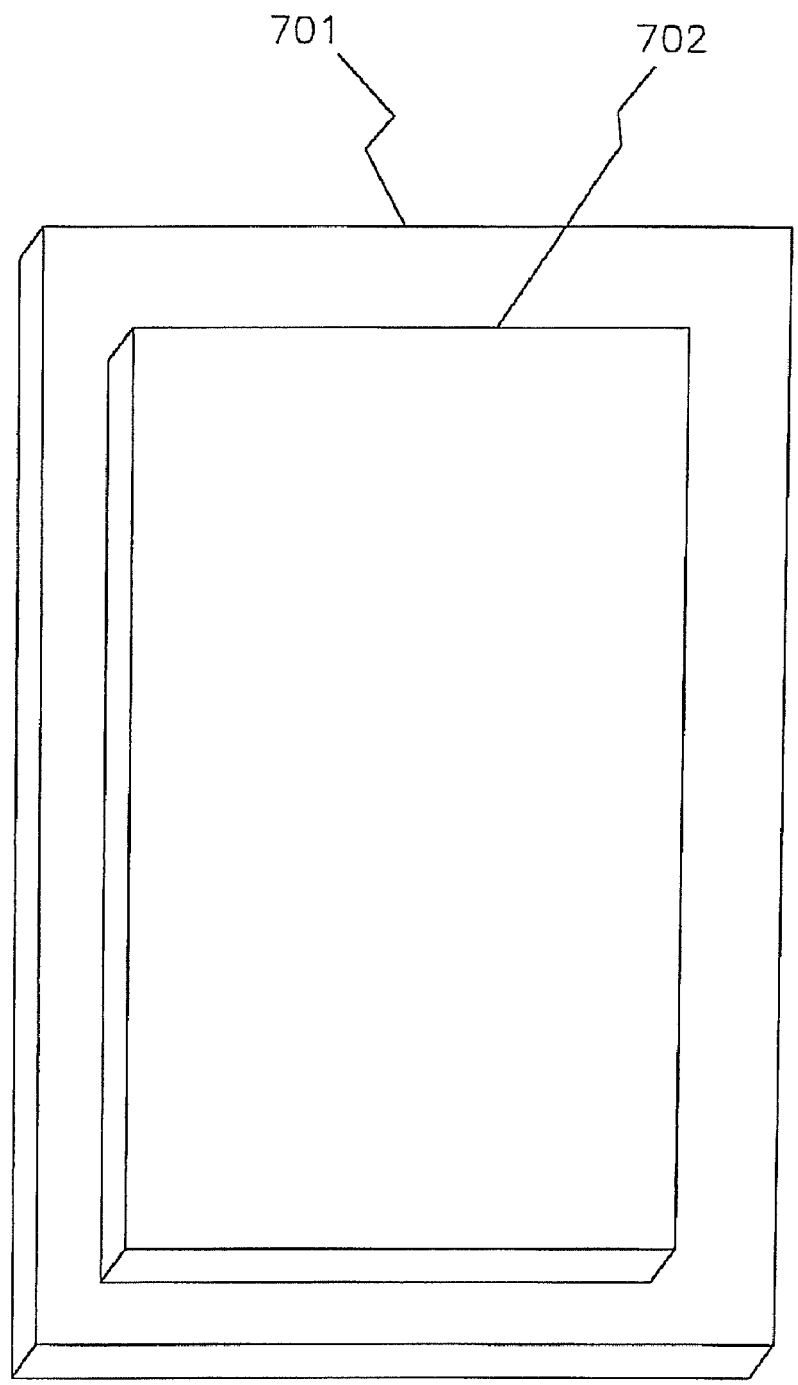
FIG. 7 shows the corresponding indifferent electrode for monopolar electrodes.

FIG. 6a illustrates a set of round monopolar electrodes (602) on a substrate material (601). FIG. 7 shows the corresponding indifferent electrode (702) for these monopolar electrodes, on a substrate (701), which may be the back of (601). FIG. 6b shows a bipolar arrangement of electrodes, both looking down onto the plane of the electrodes, positive (610) and negative (611), and also looking at the electrodes sideways to that view, positive (610) and negative (611), sitting on their substrate (614). Similarly for FIG. 6c where a multipole triplet is shown, with two positive electrodes (621) and one negative electrode, looking down on their substrate plane, and looking sideways to that view, also showing the substrate (614).

Epiretinal Electrode Array

Figure 8A:
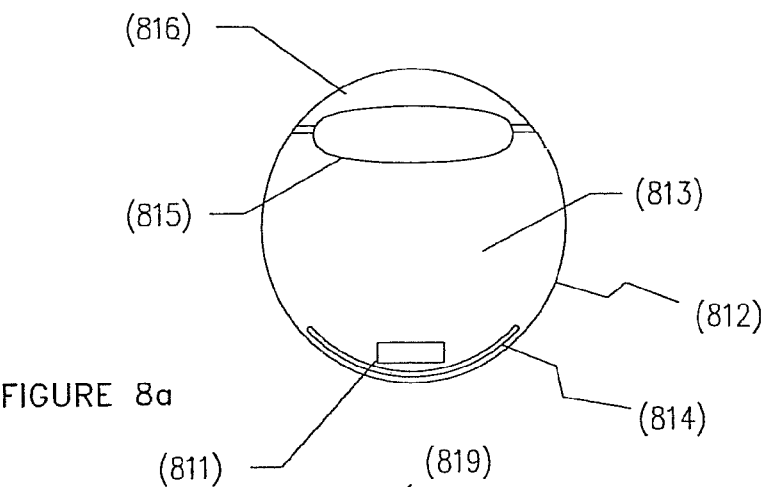
FIG. 8a depicts the location of an epiretinal electrode array located inside the eye in the vitreous humor located above the retina, toward the lens capsule and the aqueous humor.
Figure 8B:
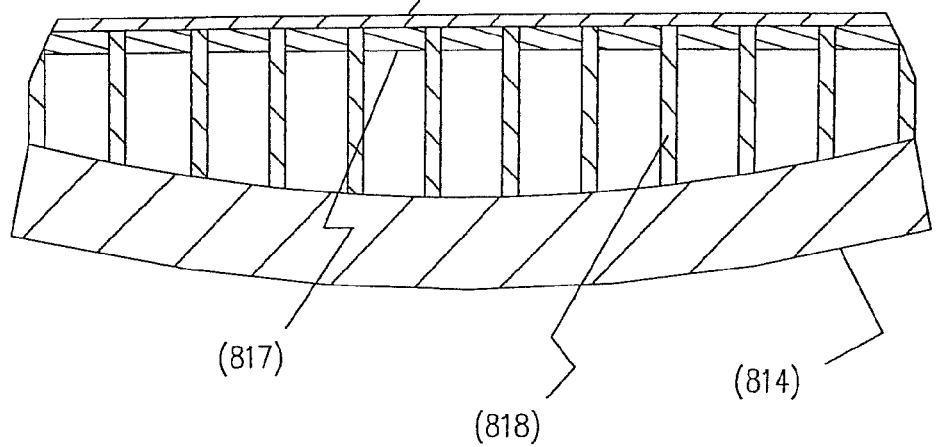
FIG. 8b shows recessed epiretinal electrodes where the electrically conducting electrodes are contained within the electrical insulation material; a silicon chip acts as a substrate; and the electrode insulator device is shaped so as to contact the retina in a conformal manner.

FIG. 8a depicts the location of an epiretinal electrode array (811) located inside the eye (812) in the vitreous humor (813) located above the retina (814), toward the lens capsule (815) and the aqueous humor (816);

One aspect of the present embodiment, shown in FIG. 8b, is the internal retinal color prosthetic part, which has electrodes (817) which may be flat conductors that are recessed in an electrical insulator (818). One flat conductor material is a biocompatible metallic foil (817). Platinum foil is a particular type of biocompatible metal foil. The electrical insulator (818) in one aspect of the embodiment is silicone.

The silicone (818) is shaped to the internal curvature of the retina (814). The vitreous humor (813), the conductive solution naturally present in the eye, becomes the effective electrode since the insulator (818) confines the field lines in a column until the current reaches the retina (814). A further advantage of this design is that the retinal tissue (814) is only in contact with the insulator (818), such as silicone, which may be more inactive, and thus, more biocompatible than the metal in the electrodes. Advantageously, another aspect of an embodiment of this invention is that adverse products produced by the electrodes (817) are distant from the retinal tissue (814) when the electrodes are recessed.

Figure 8C:
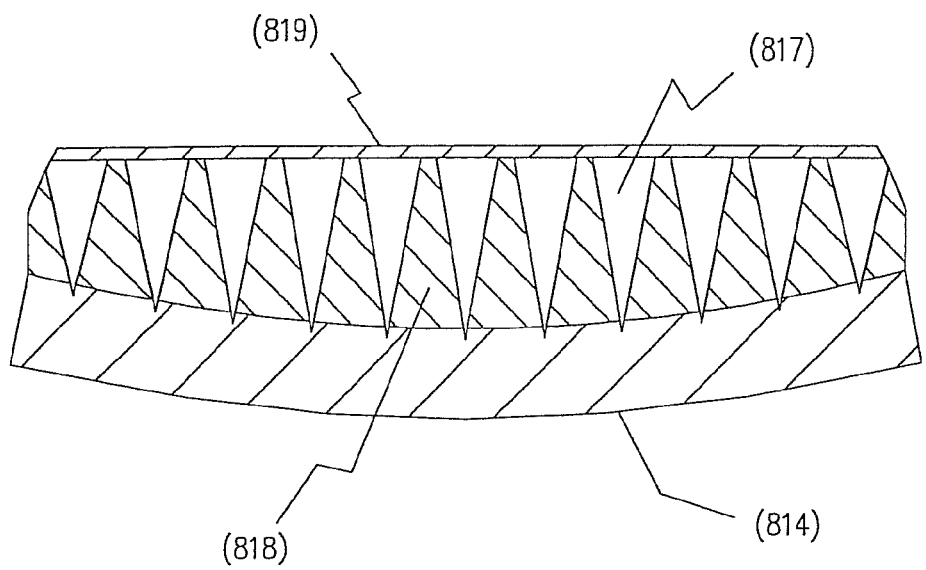
FIG. 8c is a rendering of an elongated epiretinal electrode array with the electrodes shown as pointed electrical conductors, embedded in an electrical insulator, where an pointed electrodes contact the retina in a conformal manner, however, elongated into the retina.

FIG. 8c shows elongated epiretinal electrodes (820). The electrically conducting electrodes (820) says are contained within the electrical insulation material (818); a silicon chip (819) acts as a substrate. The electrode insulator device (818) is shaped so as to contact the retina (814) in a conformal manner.

Subretinal Electrode Array

Figure 9A:
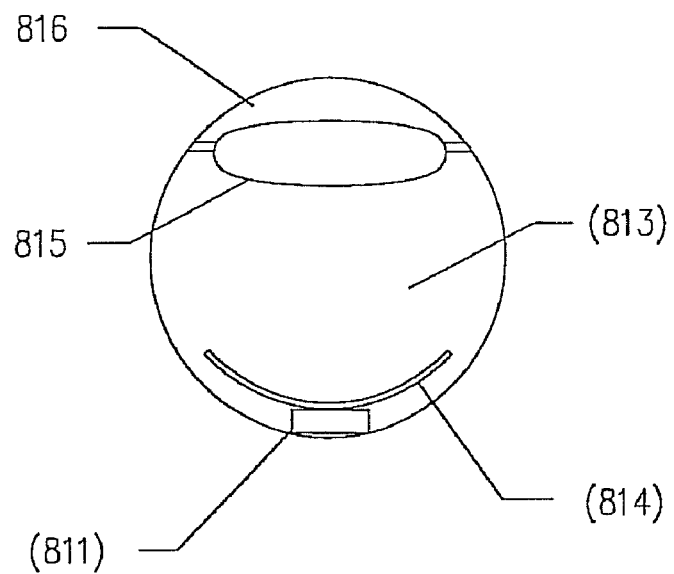
FIG. 9a shows the location of a subretinal electrode array below the retina, away from the lens capsule and the aqueous humor. The retina separates the subretinal electrode array from the vitreous humor.
Figure 9B:
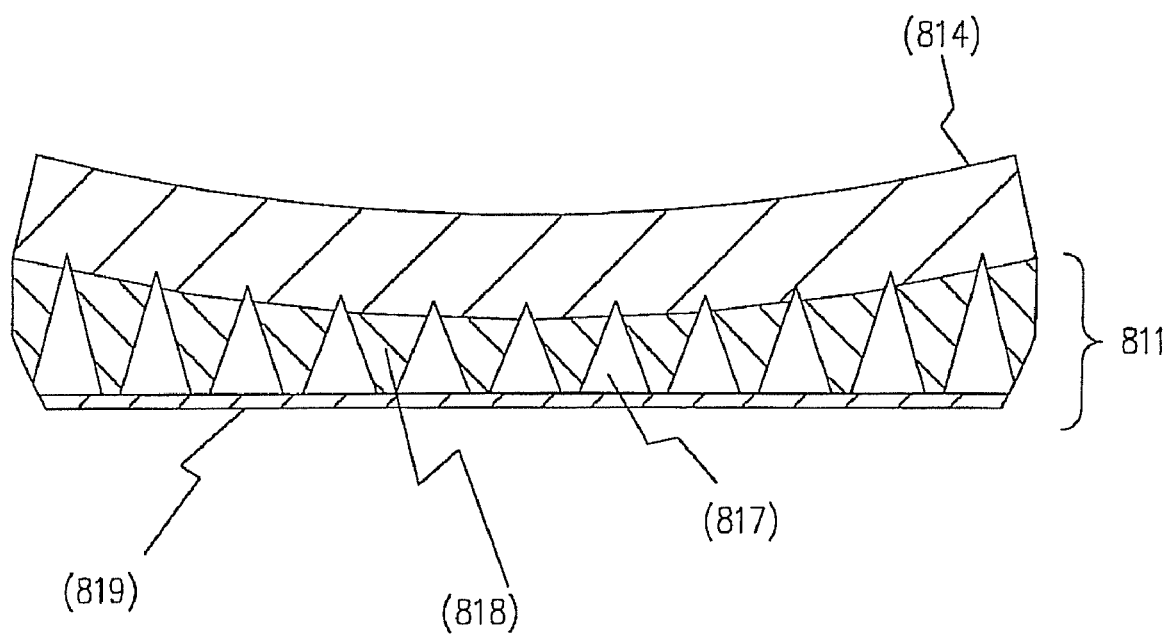
FIG. 9b illustrates the subretinal electrode array with pointed elongated electrode, the insulator, and the silicon chip substrate where the subretinal electrode array is in conformal contact with the retina with the electrodes elongated to some depth.

FIG. 9a shows the location of a subretinal electrode array (811) below the retina (814), away from the lens capsule (815) and the aqueous humor (816). The retina (814) separates the subretinal electrode array from the vitreous humor (813). FIG. 9b illustrates the subretinal electrode array (811) with pointed elongated electrodes (817), the insulator (818), and the silicon chip (819) substrate. The subretinal electrode array (811) is in conformal contact with the retina (814) with the electrodes (817) elongated to some depth.

Electrodes

Iridium Electrodes

Figure 10:
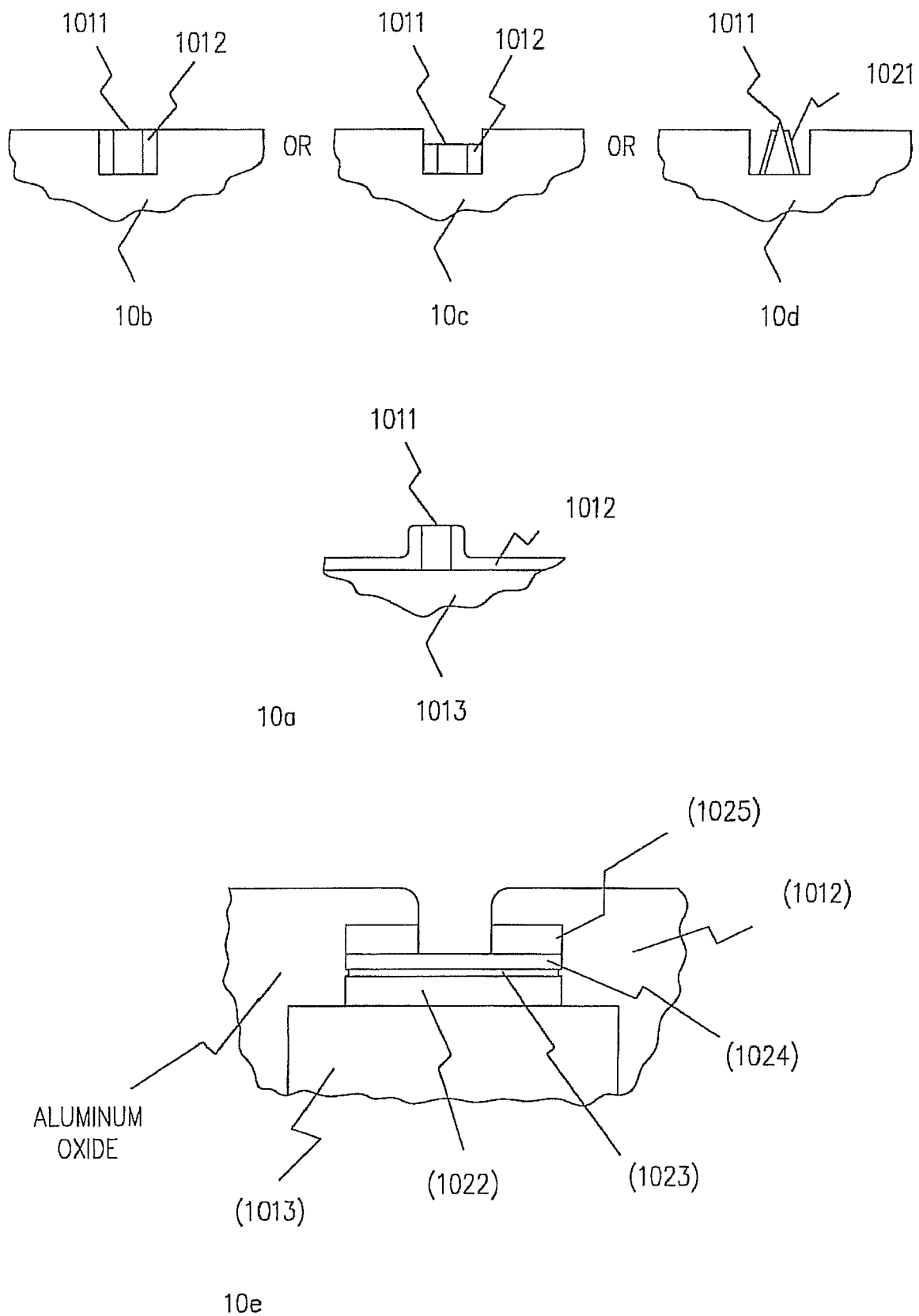
FIG. 10a shows a iridium electrode that comprises a iridium slug, an insulator, and a device substrate where this embodiment shows the iridium slug electrode flush with the extent of the insulator.
FIG. 10b indicates an embodiment similar to that shown in FIG. 10/12a, however, the iridium slug is recessed from the insulator along its sides, but with its top flush with the insulator.
FIG. 10c shows an embodiment with the iridium slug as in FIG. 10/12b; however, the top of the iridium slug is recessed below the level of the insulator.
FIG. 10d indicates an embodiment with the iridium slug coming to a point and insulation along its sides, as well as a being within the overall insulation structure.
FIG. 10e indicates an embodiment of a method for fabricating and the fabricated iridium electrode where on a substrate of silicon an aluminum pad is deposited; on the pad the conductive adhesive is laid and platinum or iridium foil is attached thereby; a titanium ring is placed, sputtered, plated, ion implanted, ion beam assisted deposited (IBAD) or otherwise attached to the platinum or iridium foil; silicon carbide, diamond-like coating, silicon nitride and silicon oxide in combination, titanium oxide, tantalum oxide, aluminum nitride, aluminum oxide or zirconium oxide or other insulator will adhere better to the titanium while it would not adhere as well to the platinum or iridium foil.

Now FIG. 10 will illuminate structure and manufacture of iridium electrodes (FIGS. 10a-e). FIG. 10a shows an iridium electrode, which comprises an iridium slug (1011), an insulator (1012), and a device substrate (1013). This embodiment shows the iridium slug electrode flush with the extent of the insulator. FIG. 10b indicates an embodiment similar to that shown in FIG. 10a, however, the iridium slug (1011) is recessed from the insulator (1012) along its sides, but with its top flush with the insulator. When the iridium electrodes (1011) are recessed in the insulating material (1012), they may have the sides exposed so as to increase the effective surface area without increasing geometric area of the face of the electrode. If an electrode (1011) is not recessed it may be coated with an insulator (1012), on all sides, except the flat surface of the face (1011) of the electrode. Such an arrangement can be embedded in an insulator that has an overall profile curvature that follows the curvature of the retina. The overall profile curvature may not be continuous, but may contain recesses, which expose the electrodes.

FIG. 10c shows an embodiment with the iridium slug as in FIG. 10b, however, the top of the iridium slug (1011) is recessed below the level of the insulator; FIG. 10d indicates an embodiment with the iridium slug (1011) coming to a point and insulation along its sides (1021), as well as a being within the overall insulation structure (1021). FIG. 10e indicates an embodiment of a method for fabricating the iridium electrodes. On a substrate (1013) of silicon, an aluminum pad (1022) is deposited. On the pad the conductive adhesive (1023) is laid and platinum or iridium foil (1024) is attached thereby. A titanium ring (1025) is placed, sputtered, plated, ion implanted, ion beam assisted deposited (IBAD) or otherwise attached to the platinum or iridium foil (1024). Silicon carbide, diamond-like coating, silicon nitride and silicon oxide in combination, titanium oxide, tantalum oxide, aluminum nitride, aluminum oxide or zirconium oxide (1012) or other insulator can adhere better to the titanium (1025) while it would not otherwise adhere as well to the platinum or iridium foil (1024). The depth of the well for the iridium electrodes ranges from 0.1 μm to 1 mm.

Elongated Electrodes

Another aspect of an embodiment of the invention is the elongated electrode, which are designed to stimulate deeper retinal cells, in one embodiment, by penetrating the retina. By getting closer to the target cells for stimulation, the current required for stimulation is lower and the focus of the stimulation is more localized. The lengths chosen are 100 microns through 500 microns, including 300 microns. FIG. 8c is a rendering of an elongated epiretinal electrode array with the electrodes shown as pointed electrical conductors (820), embedded in an electrical insulator (818), where the elongated electrodes (817) contact the retina in a conformal manner, however, penetrating into the retina (814).

These elongated electrodes, in an aspect of this of an embodiment of the invention may be of all the same length. In a different aspect of an embodiment, they may be of different lengths. Said electrodes may be of varying lengths (FIG. 8, 817), such that the overall shape of said electrode group conforms to the curvature of the retina (814). In either of these cases, each may penetrate the retina from an epiretinal position (FIG. 8a, 811), or, in a different aspect of an embodiment of this invention, each may penetrate the retina from a subretinal position (FIG. 9b, 817).

One method of making the elongated electrodes is by electroplating with one of an electrode material, such that the electrode, after being started, continuously grows in analogy to a stalagmite or stalactite. The elongated electrodes are 100 to 500 microns in length, the thickness of the retina averaging 200 microns. The electrode material is a substance selected from the group consisting of pyrolytic carbon, titanium nitride, platinum, iridium oxide, and iridium. The insulating material for the electrodes is a substance selected from the group silicon carbide, diamond-like coating, silicon nitride and silicon oxide in combination, titanium oxide, tantalum oxide, aluminum nitride, aluminum oxide or zirconium oxide.

Platinum Electrodes

FIG. 11 (a-e) demonstrates a preferred structure of, and method of, making, spiked and mushroom platinum electrodes. Examining FIG. 11a one sees that the support for the flat electrode (1103) and other components such as electronic circuits (not shown) is the silicon substrate (1101). An aluminum pad (1102) is placed where an electrode or other component is to be placed. In order to hermetically seal-off the aluminum and silicon from any contact with biological activity, a metal foil (1103), such as platinum or iridium, is applied to the aluminum pad (1102) using conductive adhesive (1104). Electroplating is not used since a layer formed by electroplating, in the range of the required thinness, has small-scale defects or holes which destroy the hermetic character of the layer. A titanium ring (1105) is next placed on the platinum or iridium foil (1103). Normally, this placement is by ion implantation, sputtering or ion beam assisted deposition (IBAD) methods. Silicon carbide, diamond-like coating, silicon nitride and silicon oxide in combination, titanium oxide, tantalum oxide, aluminum nitride, aluminum oxide or zirconium oxide (1106) is placed on the silicon substrate (1101) and the titanium ring (1105). In one embodiment, an aluminum layer (1107) is plated onto exposed parts of the titanium ring (1105) and onto the silicon carbide, diamond-like coating, silicon nitride and silicon oxide in combination, titanium oxide, tantalum oxide, aluminum nitride, aluminum oxide or zirconium oxide (1106). In this embodiment the aluminum (1107) layer acts as an electrical conductor. A mask (1108) is placed over the aluminum layer (1107).

In forming an elongated, non-flat, electrode (FIG. 11*b*), platinum is electroplated onto the platinum or iridium foil (1103). Subsequently, the mask (1108) is removed and insulation (1110) is applied over the platinum electrode (1109).

Figure 11A:
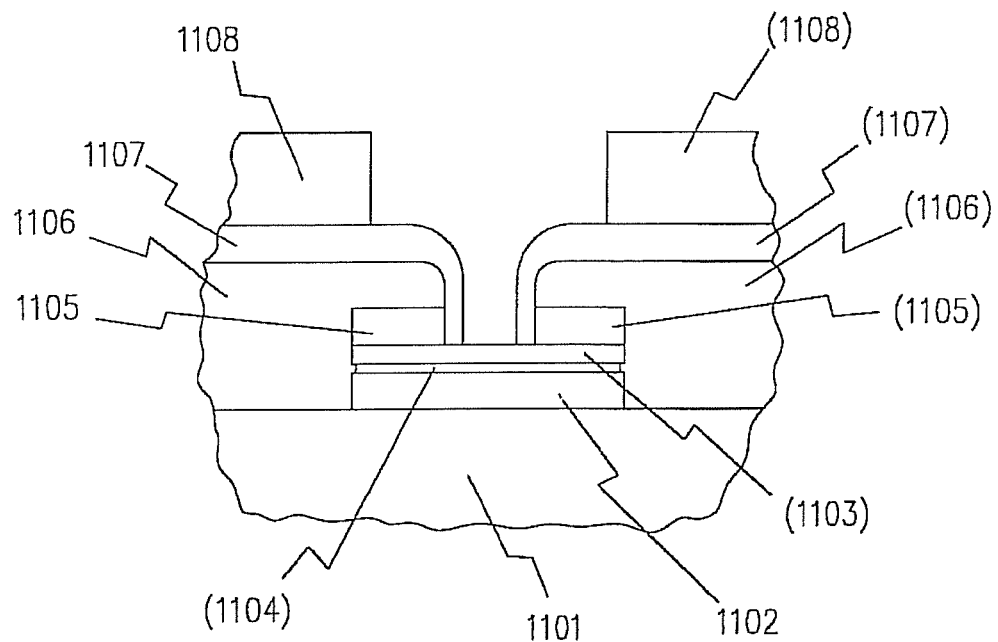
FIG. 11a depicts a preferred electrode where it is formed on a silicon substrate and makes use of an aluminum pad, a metal foil such as platinum or iridium, conductive adhesive, a titanium ring, aluminum or zirconium oxide, an aluminum layer, and a mask.
Figure 11B:
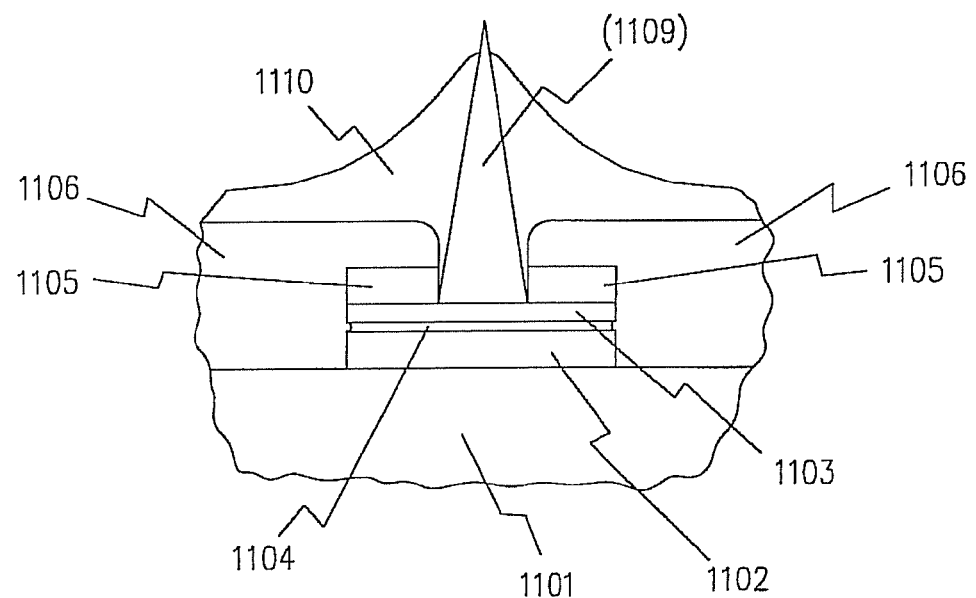
FIG. 11b shows an elongated electrode formed on the structure of FIG. 11a with platinum electroplated onto the metal foil, the mask removed and insulation applied over the platinum electrode.
Figure 11C:
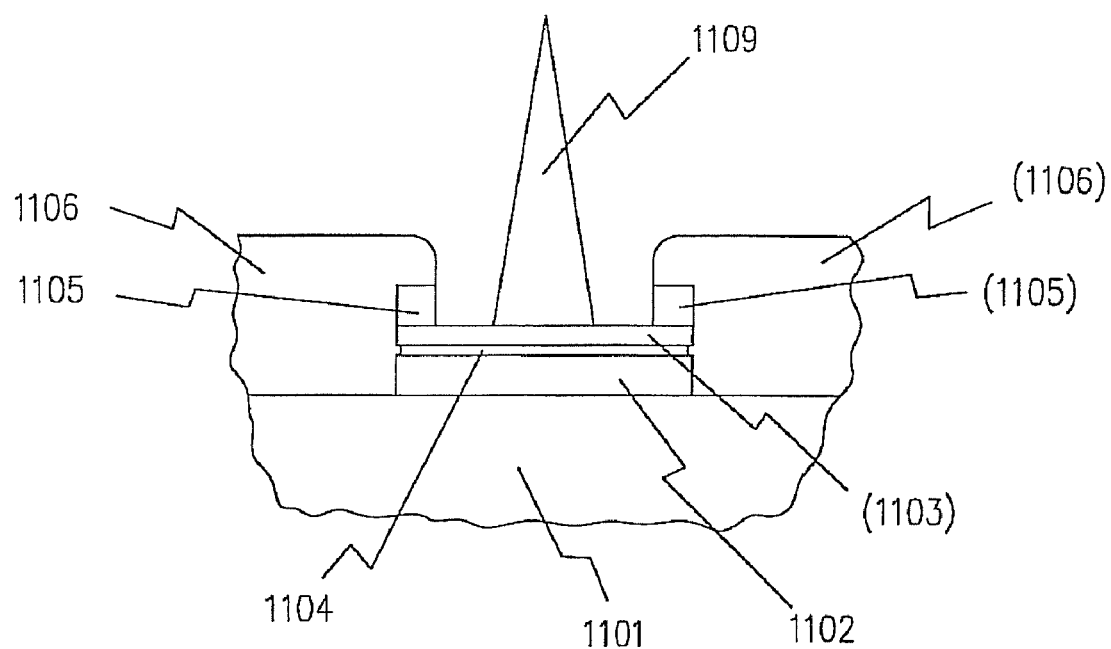
FIG. 11c shows a variation of a form of the elongated electrode wherein the electrode is thinner and more recessed from the well sides.
Figure 11D:
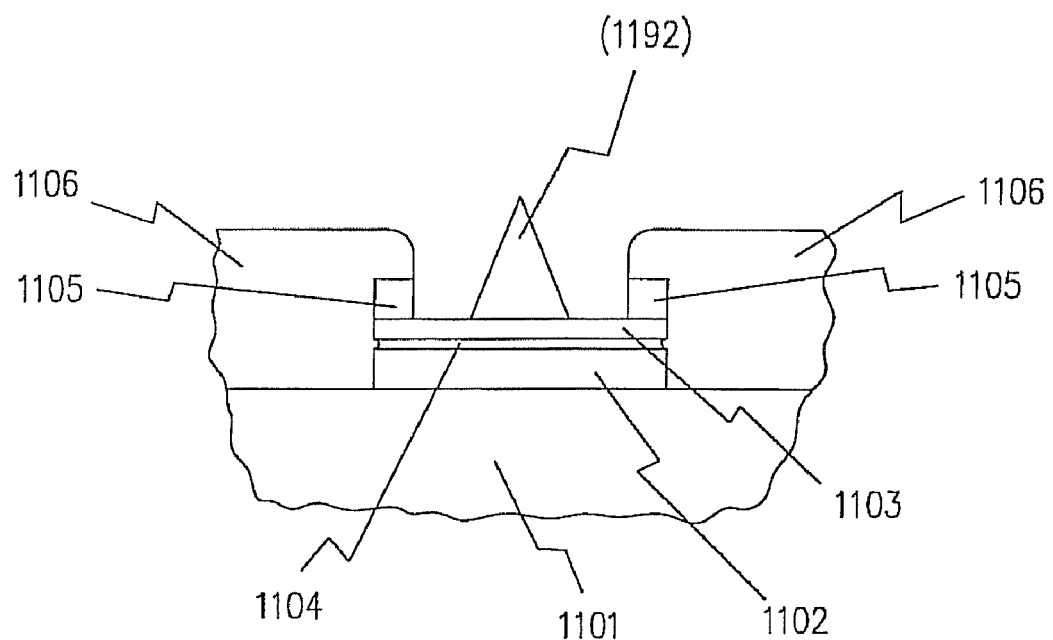
FIG. 11d shows a variation of a form of the elongated electrode wherein the electrode is squatter but recessed from the well sides.
Figure 11E:
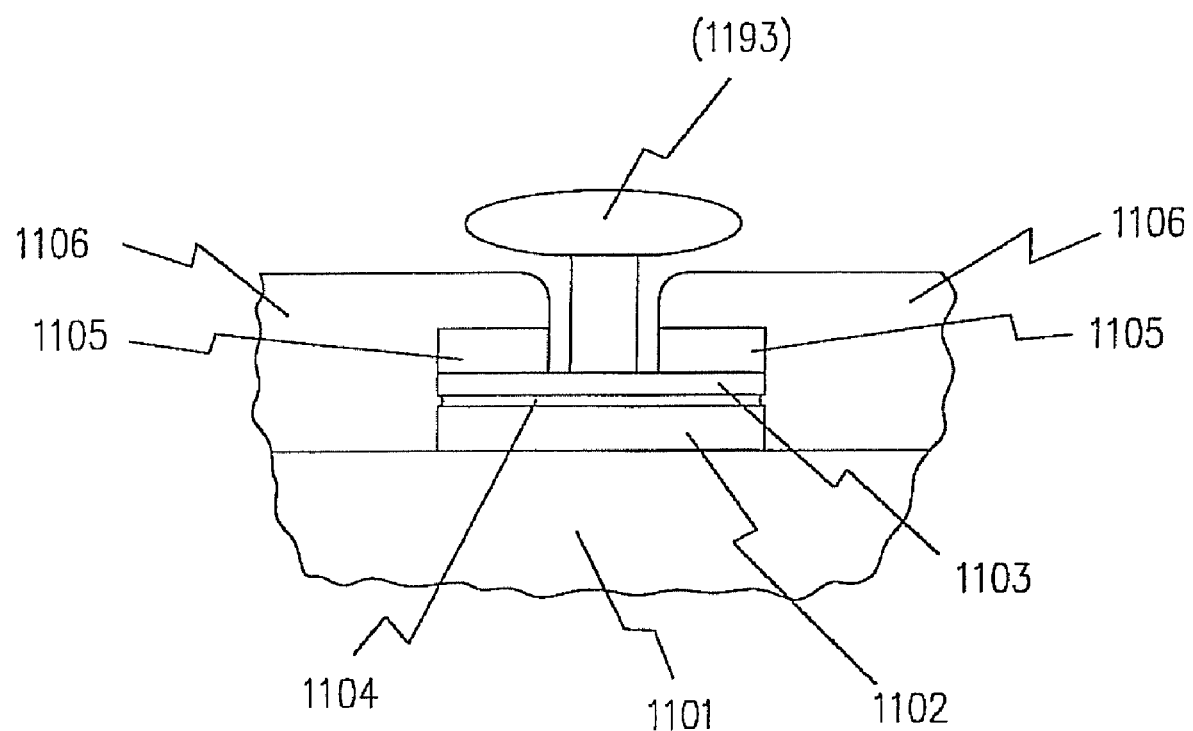
FIG. 11e shows a variation of a form of the elongated electrode wherein the electrode is a mushroom shape with the sides of its tower recessed from the well sides and its mushroom top above the oxide insulating material.

In FIG. 11*c*, a platinum electrode (1109) is shown which is more internal to the well formed by the silicon carbide, diamond-like coating, silicon nitride and silicon oxide in combination, titanium oxide, tantalum oxide, aluminum nitride, aluminum oxide or zirconium oxide and its titanium ring. The electrode (1109) is also thinner and more elongated and more pointed. FIG. 11*d* shows a platinum electrode formed by the same method as was used in FIGS. 11*a*, 11*b*, and 11*c*. The platinum electrode (1192) is more internal to the well formed by the silicon carbide, diamond-like coating, silicon nitride and silicon oxide in combination, titanium oxide, tantalum oxide, aluminum nitride, aluminum oxide or zirconium oxide and its titanium ring as was the electrode (1109) in FIG. 11*c*. However it is less elongated and less pointed.

The platinum electrode is internal to the well formed by the silicon carbide, diamond-like coating, silicon nitride and silicon oxide in combination, titanium oxide, tantalum oxide, aluminum nitride, aluminum oxide or zirconium oxide and its titanium ring; said electrode whole angle at it's peak being in the range from 1° to 120°; the base of said conical or pyramidal electrode ranging from 1 micron to 500 micron; the linear section of the well unoccupied by said conical or pyramidal electrode ranging from zero to one-third.

A similar overall construction is depicted in FIG. 1*e*. The electrode (1193), which may be platinum, is termed a mushroom shape. The maximum current density for a given metal is fixed. The mushroom shape presents a relatively larger area than a conical electrode of the same height. The mushroom shape advantageously allows a higher current, for the given limitation on the current density (e.g., milliamperes per square millimeter) for the chosen electrode material, since the mushroom shape provides a larger area.

Inductive Coupling Coils

Figure 12:
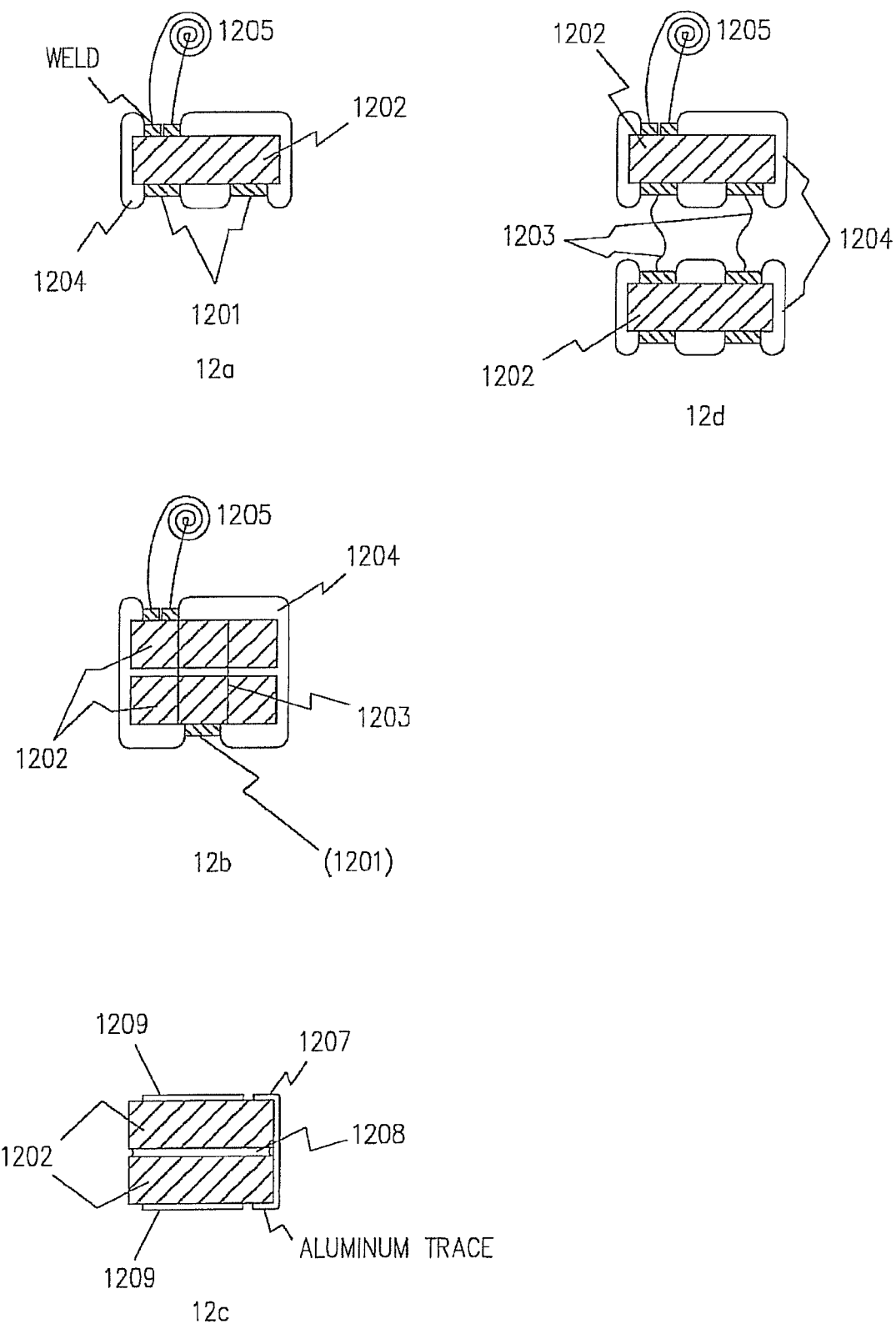
FIG. 12a shows the coil attachment to two different conducting pads at an electrode node.
FIG. 12b shows the coil attachment to two different conducting pads at an electrode node, together with two separate insulated conducting electrical pathways such as wires, each attached at two different electrode node sites on two different substrates.
FIG. 12c shows an arrangement similar to that seen in FIG. 12/16d, with the difference that the different substrates are very close with a non-conducting adhesive between them and an insulator such as aluminum or zirconium oxide forms a connection coating over the two substrates, in part.
FIG. 12d depicts an arrangement similar to that seen in FIG. 12/16c; however, the connecting wires are replaced by an externally placed aluminum conductive trace.

Information transmitted electromagnetically into or out of the implanted retinal color prosthesis utilizes insulated conducting coils so as to allow for inductive energy and signal coupling. FIG. 12*b* shows an insulated conducting coil and insulated conducting electrical pathways, e.g., wires, attached to substrates at what would otherwise be electrode nodes, with flat, recessed metallic, conductive electrodes (1201). In referring to wire or wires, insulated conducting electrical pathways are included, such as in a "two-dimensional" "on-chip" coil or a "two-dimensional" coil on a polyimide substrate, and the leads to and from these "two-dimensional" coil structures. A silicon carbide, diamond-like coating, silicon nitride and silicon oxide in combination, titanium oxide, tantalum oxide, aluminum nitride, aluminum oxide or zirconium oxide (1204) is shown acting as both an insulator and an hermetic seal. Another aspect of the embodiment is shown in FIG. 12*d*. The electrode array unit (1201) and the electronic circuitry unit (1202) can be on one substrate, or they may be on separate substrates (1202) joined by an insulated wire or by a plurality of insulated wires (1203). Said separate substrate units can be relatively near one another. For example, they might lie against a retinal surface, either epiretinally or subretinally placed. Two substrates units connected by insulated wires may carry more electrodes than if only one substrate with electrodes was employed, or it might be arranged with one substrate carrying the electrodes, the other the electronic circuitry. Another arrangement has the electrode substrate or substrates placed in a position to stimulate the retinal cells, while the electronics are located closer to the lens of the eye to avoid heating the sensitive retinal tissue.

In all of the FIGS. 12*a*, 12*b*, and 12*c*, a coil (1205) is shown attached by an insulated wire. The coil can be a coil of wire, or it can be a "two dimensional" trace as an "on-chip" component or as a component on polyimide. This coil can provide a stronger electromagnetic coupling to an outside-the-eye source of power and of signals. FIG. 12*c* shows an externally placed aluminum (conductive) trace instead of the electrically conducting wire of FIG. 12*d*. Also shown is an electrically insulating adhesive (1208) which prevents electrical contact between the substrates (1202) carrying active circuitry (1209).

Hermetic Sealing

Hermetic Coating

All structures, which are subject to corrosive action as a result of being implanted in the eye, or, those structures which are not completely biocompatible and not completely safe to the internal cells and fluids of the eye require hermetic sealing. Hermetic sealing may be accomplished by coating the object to be sealed with silicon carbide, diamond-like coating, silicon nitride and silicon oxide in combination, titanium oxide, tantalum oxide, aluminum nitride, aluminum oxide or zirconium oxide. These materials also provide electrical insulation. The method and apparatus of hermetic sealing by aluminum and zirconium oxide coating is described in a pending U.S. patent application Ser. No. 08/994,515, now U.S. Pat. No. 6,043,437. The methods of coating a substrate material with the hermetic sealant include sputtering, ion implantation, and ion-beam assisted deposition (IBAD).

Hermetic Box

Figure 13:
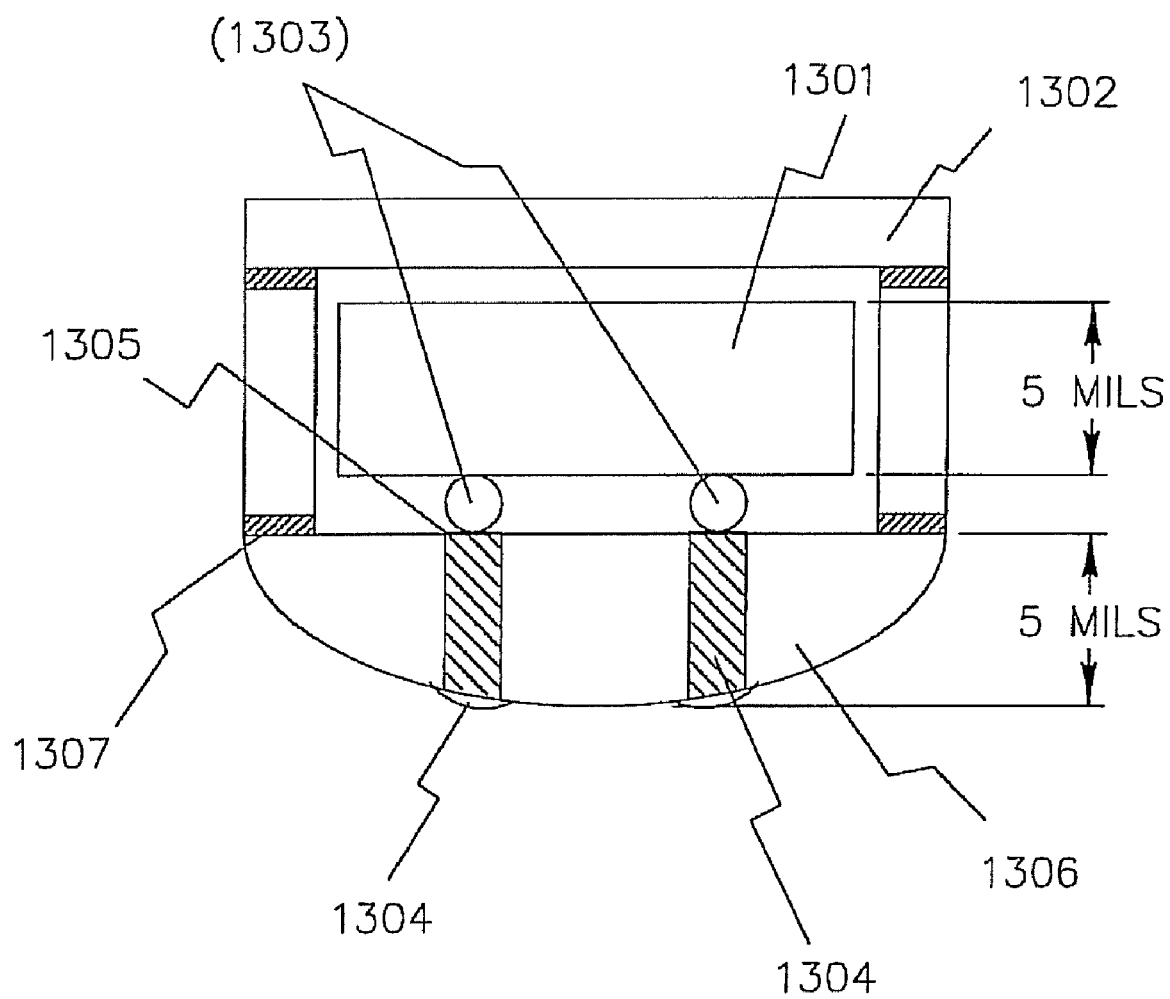
FIG. 13 shows a hermetically sealed flip-chip in a ceramic or glass case with solder ball connections to hermetically sealed glass frit and metal leads.

Another aspect of an embodiment of the invention is hermetically sealing the silicon chip (1301) by placing it in a metal or ceramic box (1302) of rectangular cross-section with the top and bottom sides initially open (FIG. 13). The box may be of one (1302) of the metals selected from the group comprising platinum, iridium, palladium, gold, and stainless steel. Solder balls (1303) are placed on the "flip-chip", i.e., a silicon-based chip that has the contacts on the bottom of the chip (1301). Metal feedthroughs (1304) made from a metal selected from the group consisting of radium, platinum, titanium, iridium, palladium, gold, and stainless steel. The bottom cover (1306) is formed from one of the ceramics selected from the group consisting of aluminum oxide or zirconium oxide. The inner surface (1305), toward the solder ball, (1303)) of the feed-through (1304) is plated with gold or with nickel. The ceramic cover (1306) is then attached to the box using a braze (1307) selected from the group consisting of: 50% titanium together with 50% nickel and gold. Electronics are then inserted and the metal top cover (of the same metal selected for the box) is laser welded in place.

Separate Electronics Chip Substrate and Electrode Substrate

Figure 14:
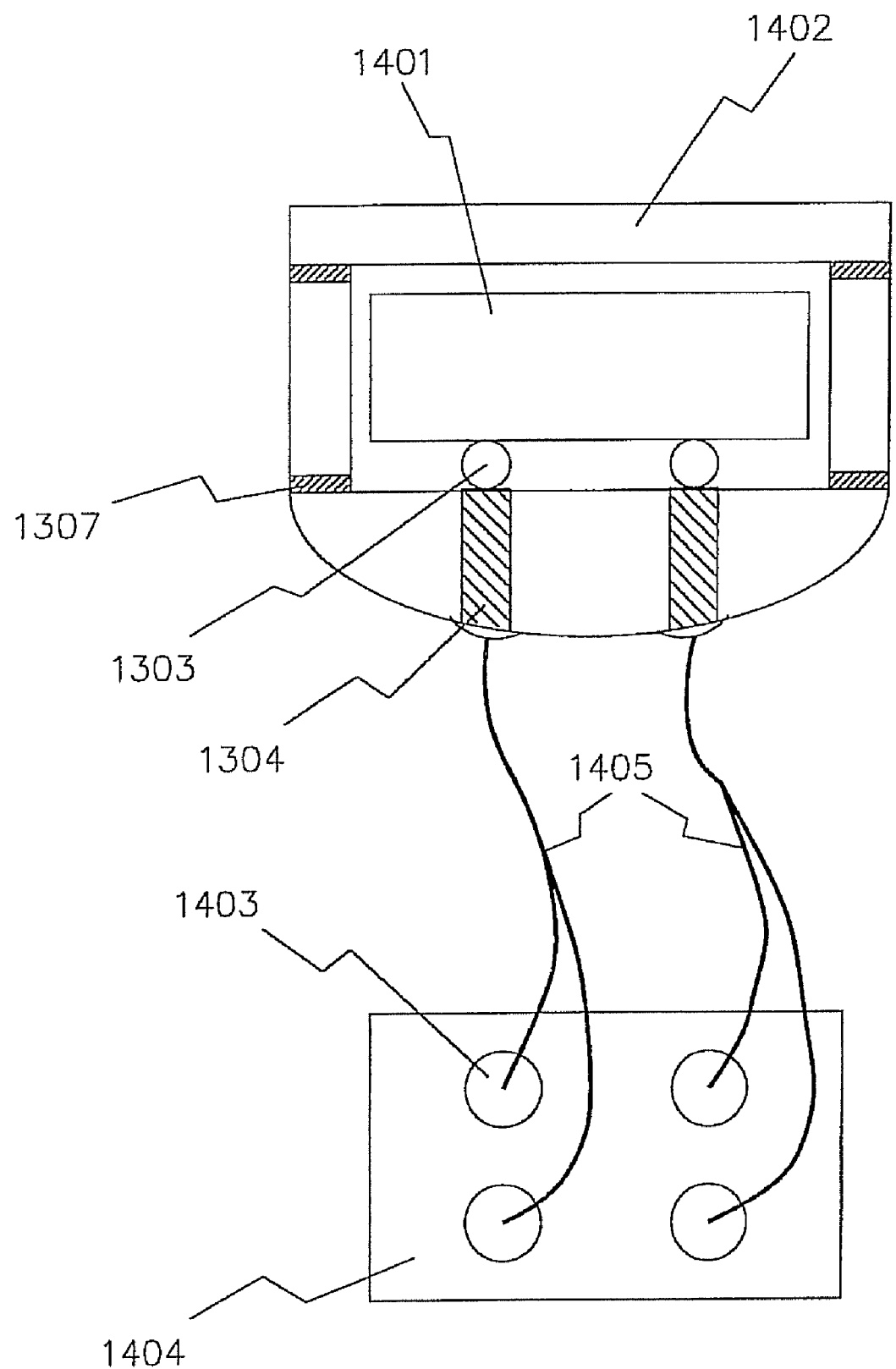
FIG. 14 shows a hermetically sealed electronic chip as in FIG. 18 with the addition of biocompatible leads to pads on a remotely located electrode substrate.

In one embodiment of the invention (FIG. 14), the chip substrate (1401) is hermetically sealed in a case (1402) or by a coating of the aluminum, zirconium, or magnesium oxide coating. However, the electrodes (1403) and its substrate (1404) form a distinct and separate element. Insulated and hermetically sealed wires (1405) connect the two. The placement of the electrode element may be epiretinal, while the electronic chip element may be relatively distant from the electrode element, as much distant as being in the vicinity of the eye lens. Another embodiment of the invention has the electrode element placed subretinally and the electronic chip element placed toward the rear of the eye, being outside the eye, or, being embedded in the sclera of the eye or in or under the choroid, blood support region for the retina. Another embodiment of the invention has the electronic chip element implanted in the fatty tissue behind the eye and the electrode element placed subretinally or epiretinally.

Capacitive Electrodes

A plurality of capacitive electrodes can be used to stimulate the retina, in place of non-capacitive electrodes. A method of fabricating said capacitive electrode uses a pair of substances selected from the pair group consisting of the pairs iridium and iridium oxide; and, titanium and titanium nitride. The metal electrode acts with the insulating oxide or nitride, which typically forms of its own accord on the surface of the electrode. Together, the conductor and the insulator form an electrode with capacitance.

Figure 15:
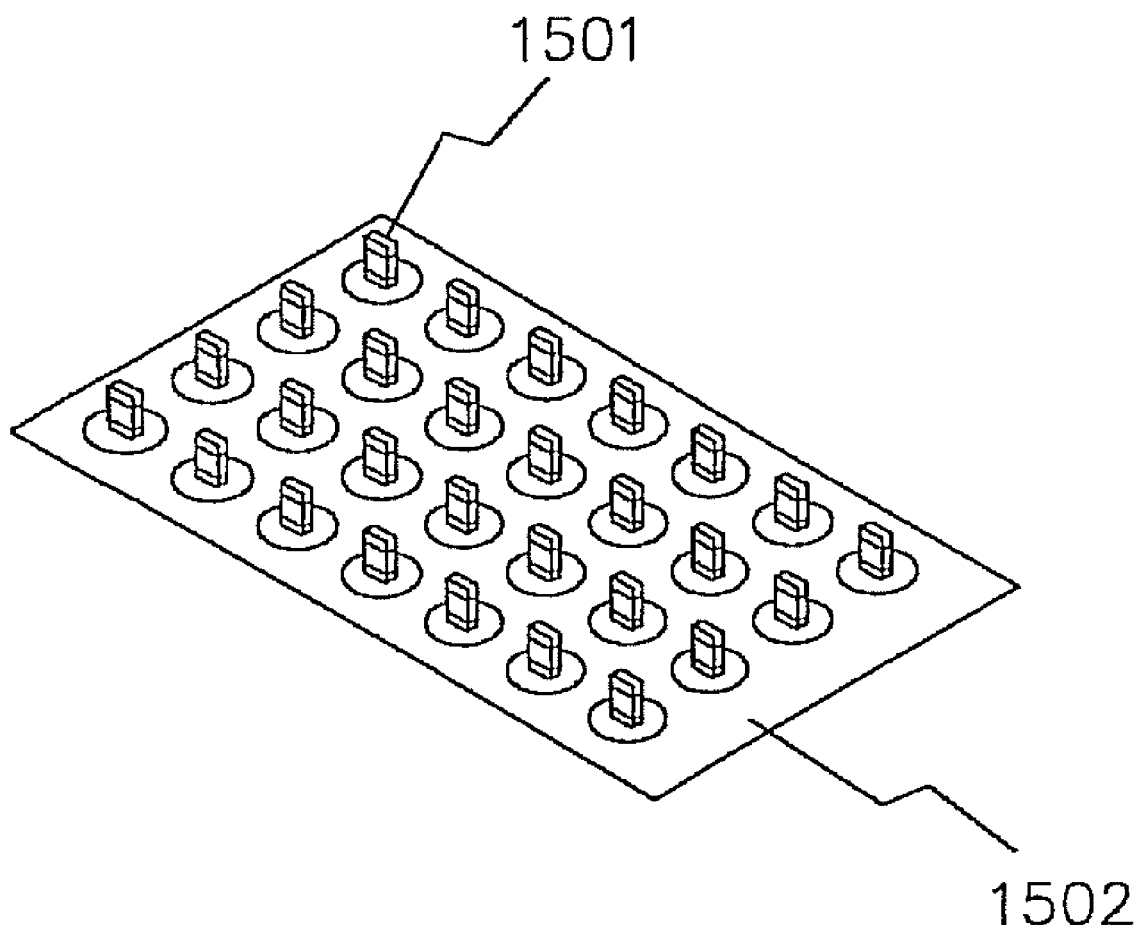
FIG. 15 shows discrete capacitors on the electrode-opposite side of an electrode substrate.

Mini-capacitors (FIG. 15) can also be used to supply the required isolating capacity. The capacity of the small volume size capacitors (1501) is 0.47 microfarads. The dimensions of these capacitors are individually 20 mils (length) by 20 mils (width) by 40 mils (height). In one embodiment of the invention, the capacitors are mounted on the surface of a chip substrate (1502), that surface being opposite to the surface containing the active electronics elements of the chip substrate.

Electrode/Electronics Component Placement

Figure 16A:
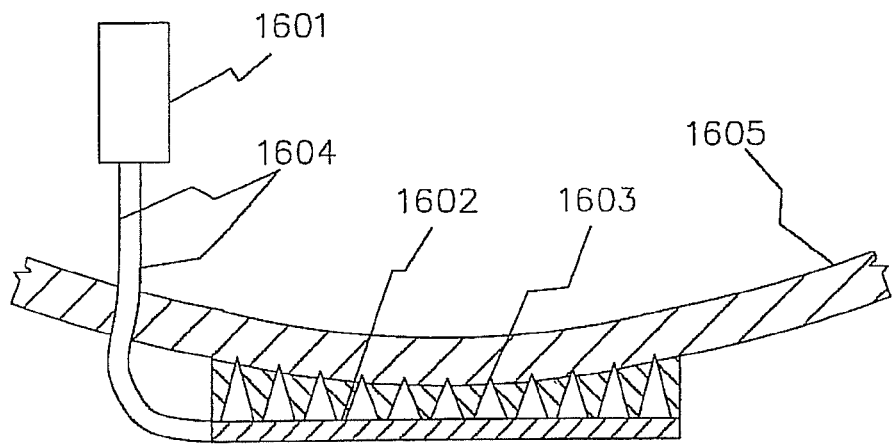
FIG. 16a shows an electrode-electronics retinal implant placed with the electrode half implanted beneath the retina, subretinally, while the electronics half projects above the retina, epiretinally.

In one embodiment (FIG. 16*a*), the internal-to-the-eye implanted part consists of two subsystems, the electrode component subretinally positioned and the electronic component epiretinally positioned. The electronics component, with its relatively high heat dissipation, is positioned at a distance, within the eye, from the electrode component placed near the retina that is sensitive to heat.

Figure 16B:
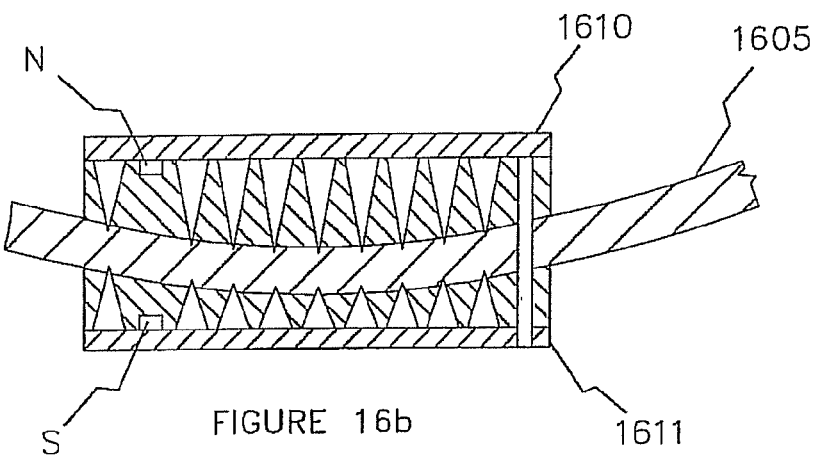
FIG. 16b shows another form of sub- and epi-retinal implantation wherein half of the electrode implant is epiretinal and half is subretinal.

An alternative embodiment shown in FIG. 16*b* is where one of the combined electronic and electrode substrate units is positioned subretinally and the other is located epiretinally and both are held together across the retina so as to efficiently stimulate bipolar and associated cells in the retina.

An alternative embodiment of the invention has the electronic chip element implanted in the fatty tissue behind the eye and the electrode element placed subretinally or epiretinally, and power and signal communication between them by electromagnetic means including radio-frequency (RF), optical, and quasi-static magnetic fields, or by acoustic means including ultrasonic transducers.

Figure 16C:
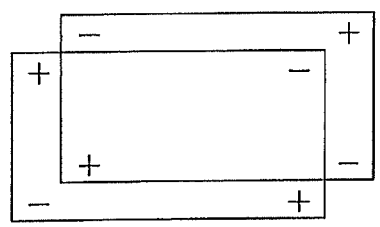
FIG. 16c shows the electrode parts are lined up by alignment pins or by very small magnets.
Figure 16D:
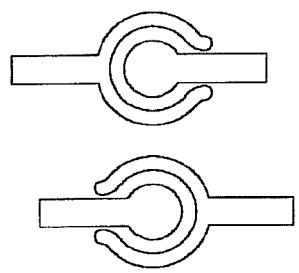
FIG. 16d shows the electrode part lined up by template shapes which may snap together to hold the parts in a fixed relationship to each other.

FIG. 16*c* shows how the two electronic-electrode substrate units are held positioned in a prescribed relationship to each other by small magnets. Alternatively the two electronic-electrode substrate units are held in position by alignment pins. Another aspect of this is to have the two electronic-electrode substrate units held positioned in a prescribed relationship to each other by snap-together mating parts, some exemplary ones being shown in FIG. 16*d*.

Neurotrophic Factor

Another aspect of the embodiment is the use of a neurotrophic factor, for example, Nerve Growth Factor, applied to the electrodes, or to the vicinity of the electrodes, to aid in attracting target nerves and other nerves to grow toward the electrodes.

Eye-Motion Compensation System

Another aspect of the embodiment is an eye-motion compensation system comprising an eye-movement tracking apparatus (FIG. 1*b*, 112); measurements of eye movement; a transmitter to convey said measurements to video data processor unit that interprets eye movement measurements as angular positions, angular velocities, and angular accelerations; and the processing of eye position, velocity, acceleration data by the video data processing unit for image compensation, stabilization and adjustment.

Ways of eye-tracking (FIG. 1*b*, 112) include utilizing the corneal eye reflex, utilizing an apparatus for measurements of electrical activity where one or more coils are located on the eye and one or more coils are outside the eye, utilizing an apparatus where three orthogonal coils placed on the eye and three orthogonal coils placed outside the eye, utilizing an apparatus for tracking movements where electrical recordings from extra-ocular muscles are measured and conveyed to the video data processing unit that interprets such electrical measurements as angular positions, angular velocities, and angular accelerations. The video data processing unit uses these values for eye position, velocity, acceleration to compute image compensation, stabilization and adjustment data which is then applied by the video data processor to the electronic form of the image.

Head Sensor

Another aspect of the embodiment utilizes a head motion sensor (131). The basic sensor in the head motion sensor unit is an integrating accelerometer. A laser gyroscope can also be used. A third sensor is the combination of an integrating accelerometer and a laser gyroscope. The video data processing unit can incorporate the data of the motion of the eye as well as that of the head to further adjust the image electronically so as to account for eye motion and head motion.

Physician's Local Control Unit

Another aspect includes a retinal prosthesis with (see FIG. 1*b*) a physician's local external control unit (115) allowing the physician to exert setup control of parameters such as amplitudes, pulse widths, frequencies, and patterns of electrical stimulation. The physician's control unit (115) is also capable of monitoring information from the implanted unit (121) such as electrode current, electrode impedance, compliance voltage, and electrical recordings from the retina. The monitoring is done via the internal telemetry unit, electrode and electronics assembly (121).

An important aspect of setting up the retinal color prosthesis is setting up electrode current amplitudes, pulse widths, and frequencies so they are comfortable for the patient. FIGS. 17*a-c* and FIGS. 18*a-c* illustrate some of the typical displays.

A computer-controlled stimulating test that incorporates patient response to arrive at optimal patient settings may be compared to being fitted for eyeglasses, first determining diopter, then cylindrical astigmatic correction, and so forth for each patient. The computer uses interpolation and extrapolation routines. Curve or surface or volume fitting of data may be used. For each pixel, the intensity in increased until a threshold is reached and the patient can detect something in his visual field. The intensity is further increased until the maximum comfortable brightness is reached. The patient determines his subjective impression of one-quarter maximum brightness, one-half maximum brightness, and three-quarters maximum brightness. Using the semi-automated processing of the patient-in-the-loop with the computer, the test program runs through the sequences and permutations of parameters and remembers the patient responses. In this way apparent brightness response curves are calibrated for each electrode for amplitude. Additionally, in the same way as for amplitude, pulse width and pulse rate (frequency), response curves are calibrated for each patient. The clinician can then determine what the best settings are for the patient.

This method is generally applicable to many, if not all, types of electrode based retinal prostheses. Moreover, it also is applicable to the type of retinal prosthesis, which uses an external light intensifier shining upon essentially a spatially distributed set of light sensitive diodes with a light activated electrode. In this latter case, a physician's test, setup and control unit is applied to the light intensifier which scans the implanted photodiode array, element by element, where the patient can give feedback and so adjust the light intensifier parameters.

Remote Physician's Unit

Another aspect of an embodiment of this invention includes (see FIG. 1b) a remote physician control unit (117) that can communicate with a patient's unit (114) over the public switched telephone network or other telephony means. This telephone-based pair of units is capable of performing all of the functions of the of the physician's local control unit (115).

Physician's Unit Measurements Menus and Displays

Both the physician's local (115) and the physician's remote (117) units always measure brightness, amplitudes, pulse widths, frequencies, patterns of stimulation, shape of log amplification curve, electrode current, electrode impedance, compliance voltage and electrical recordings from the retina.

Figure 17A:
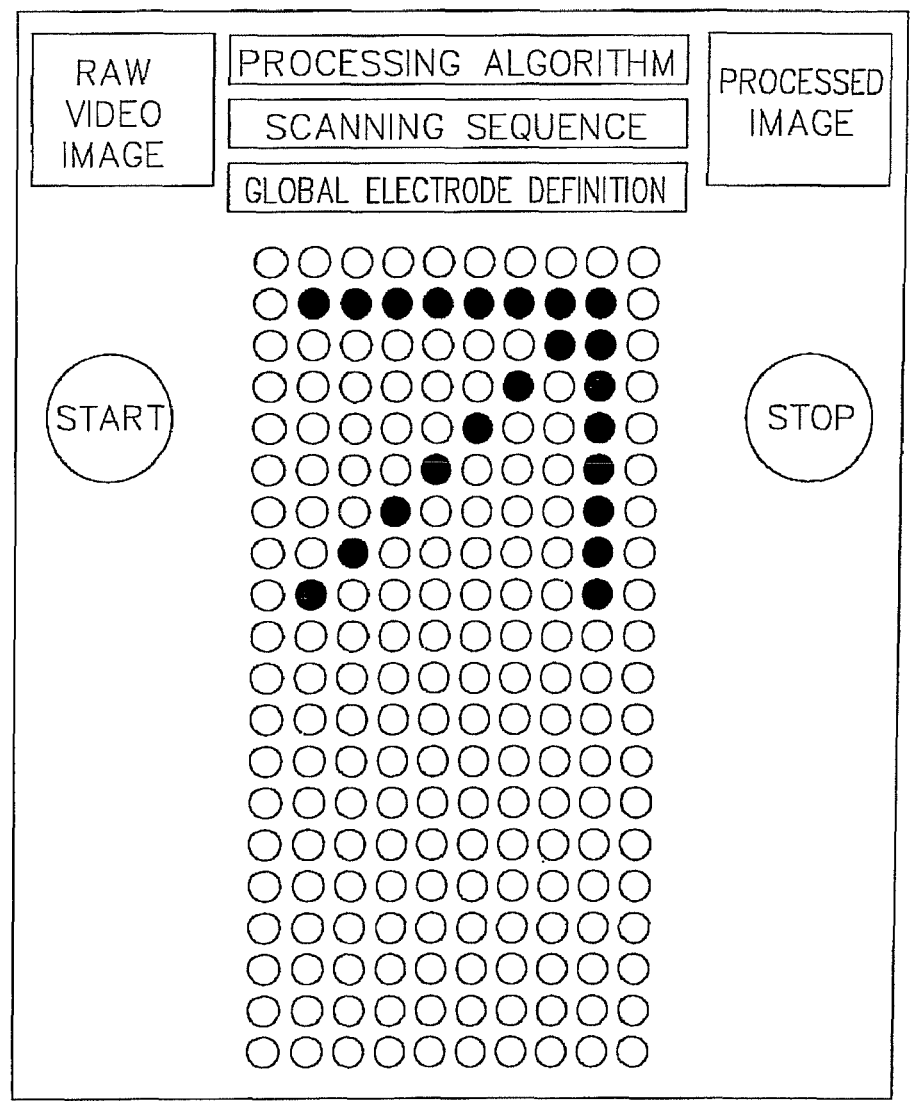
FIG. 17a shows the main screen of the physician's (local) controller (and programmer)
Figure 17B:
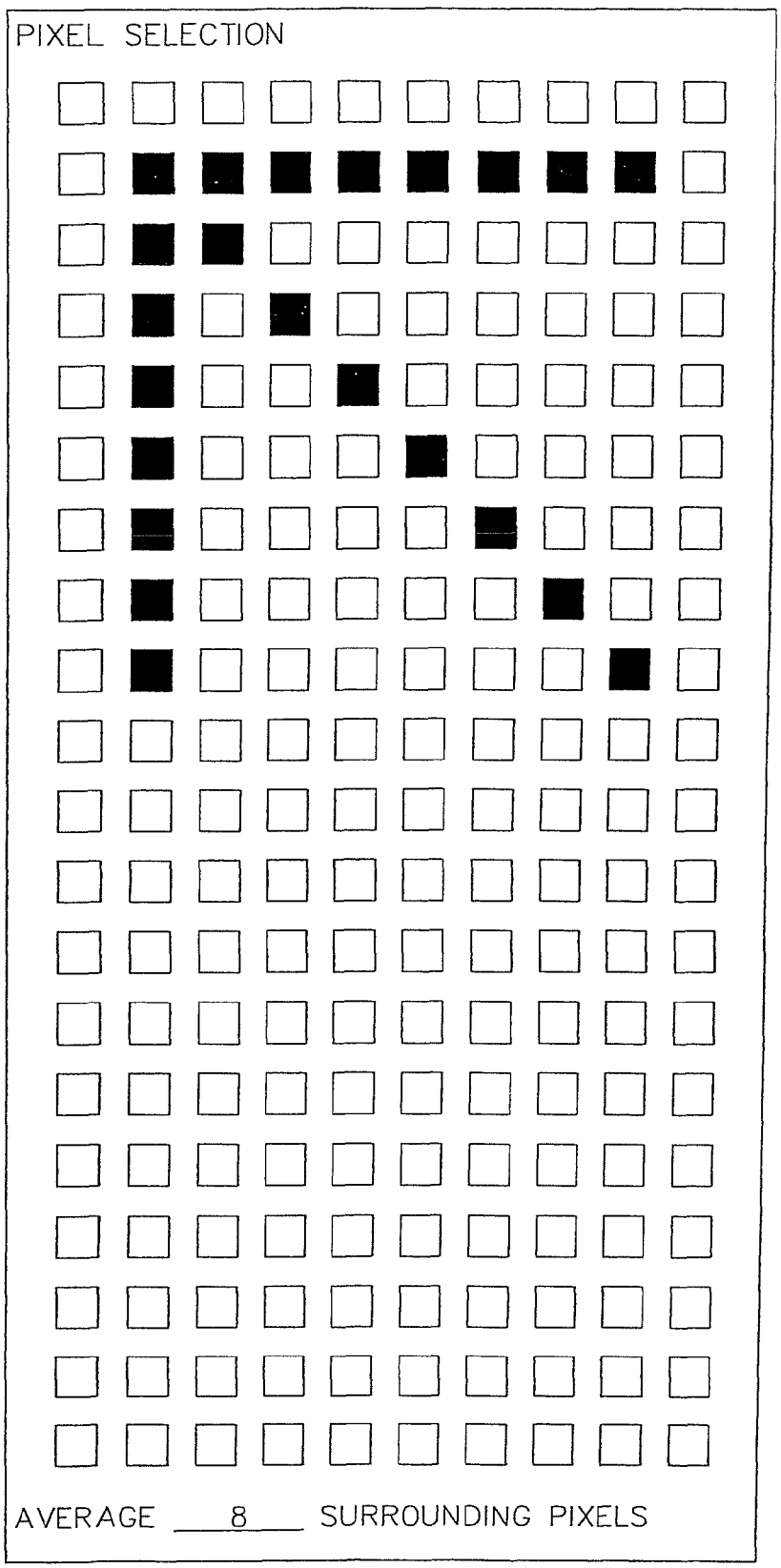
FIG. 17b illustrates the pixel selection of the processing algorithm with the averaging of eight surrounding pixels chosen as one element of the processing.

FIG. 17a shows the main screen of the Physician's Local and Remote Controller and Programmer. FIG. 17b illustrates the pixel selection of the processing algorithm with the averaging of eight surrounding pixels chosen as one element of the processing. FIG. 17c represents an electrode scanning sequence, in this case the predefined sequence, A. FIG. 17d shows electrode parameters, here for electrode B, including current amplitudes and waveform timelines. FIG. 17e illustrates the screen for choosing the global electrode configuration, monopolar, bipolar, or multipolar. FIG. 17f renders a screen showing the definition of bipolar pairs (of electrodes). FIG. 17g shows the definition of the multipole arrangements.

Figure 18A:
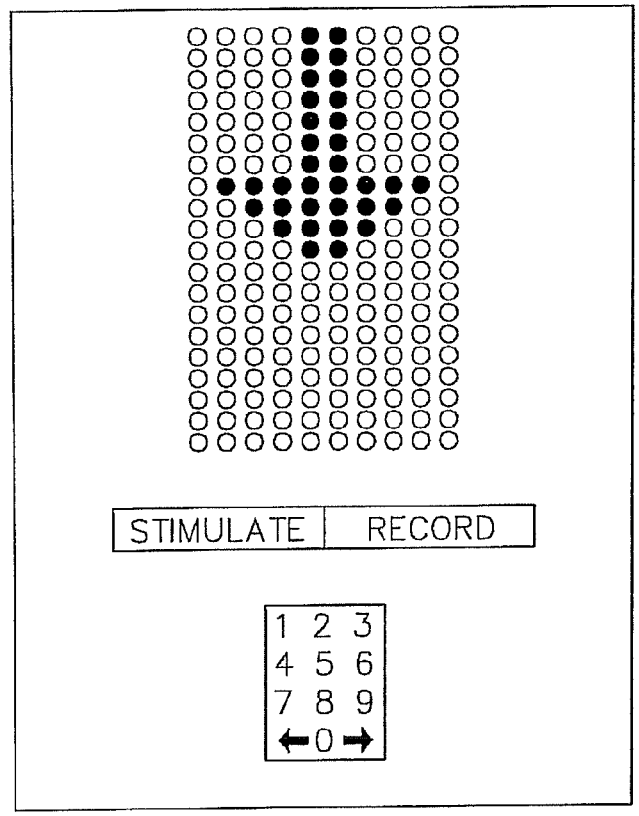
FIG. 18a illustrates the main menu screen for the palm-sized test unit.
Figures 18B, 18C:
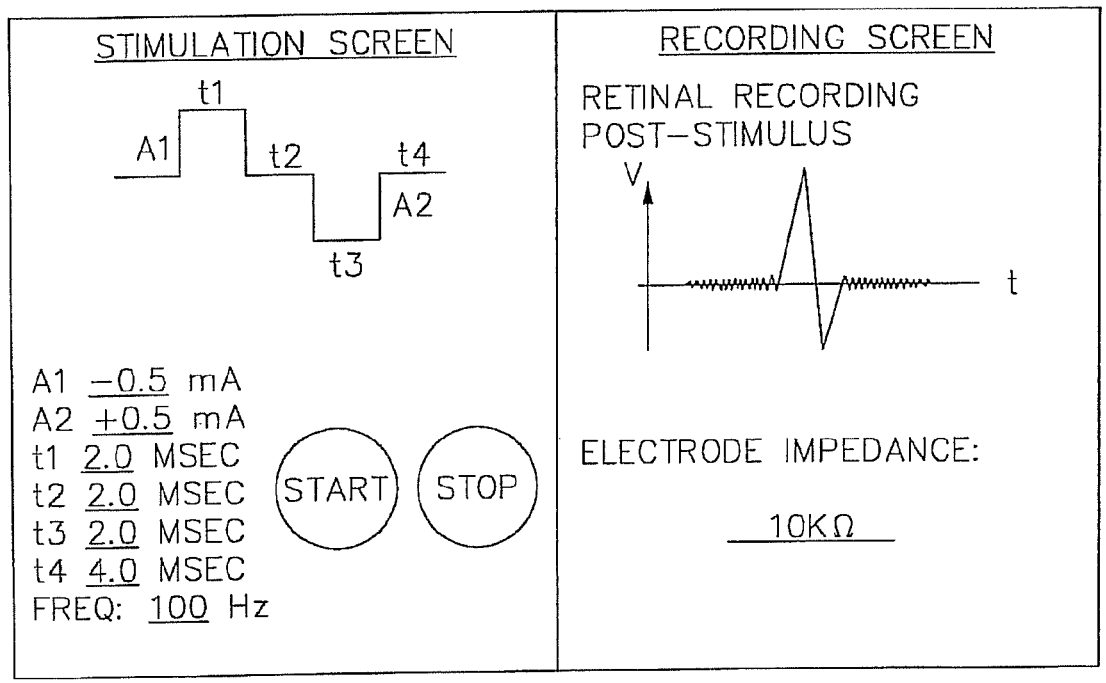
FIG. 18b shows a result of pressing on the stimulate bar of the main menu screen, where upon pressing the start button the amplitudes A1 and A2 are stimulated for times t1, t2, t3, and t4, until the stop button is pressed.
FIG. 18c exhibits a recording screen that shows the retinal recording of the post-stimulus and the electrode impedance.

FIG. 18a illustrates the main menu screen for the palm-sized test unit. FIG. 18b shows a result of pressing on the stimulate bar of the (palm-sized unit) main menu screen, where upon pressing the start button the amplitudes A1 and A2 are stimulated for times t1, t2, t3, and t4, until the stop button is pressed. FIG. 18c exhibits a recording screen that shows the retinal recording of the post-stimulus and the electrode impedance.

FIGS. 19a, 19b, and 19c show different embodiments of the Physician's Remote Controller, which has the same functionality inside as the Physician's Local Controller but with the addition of communication means such as telemetry or telephone modem.

Patient's Controller

Figure 20:
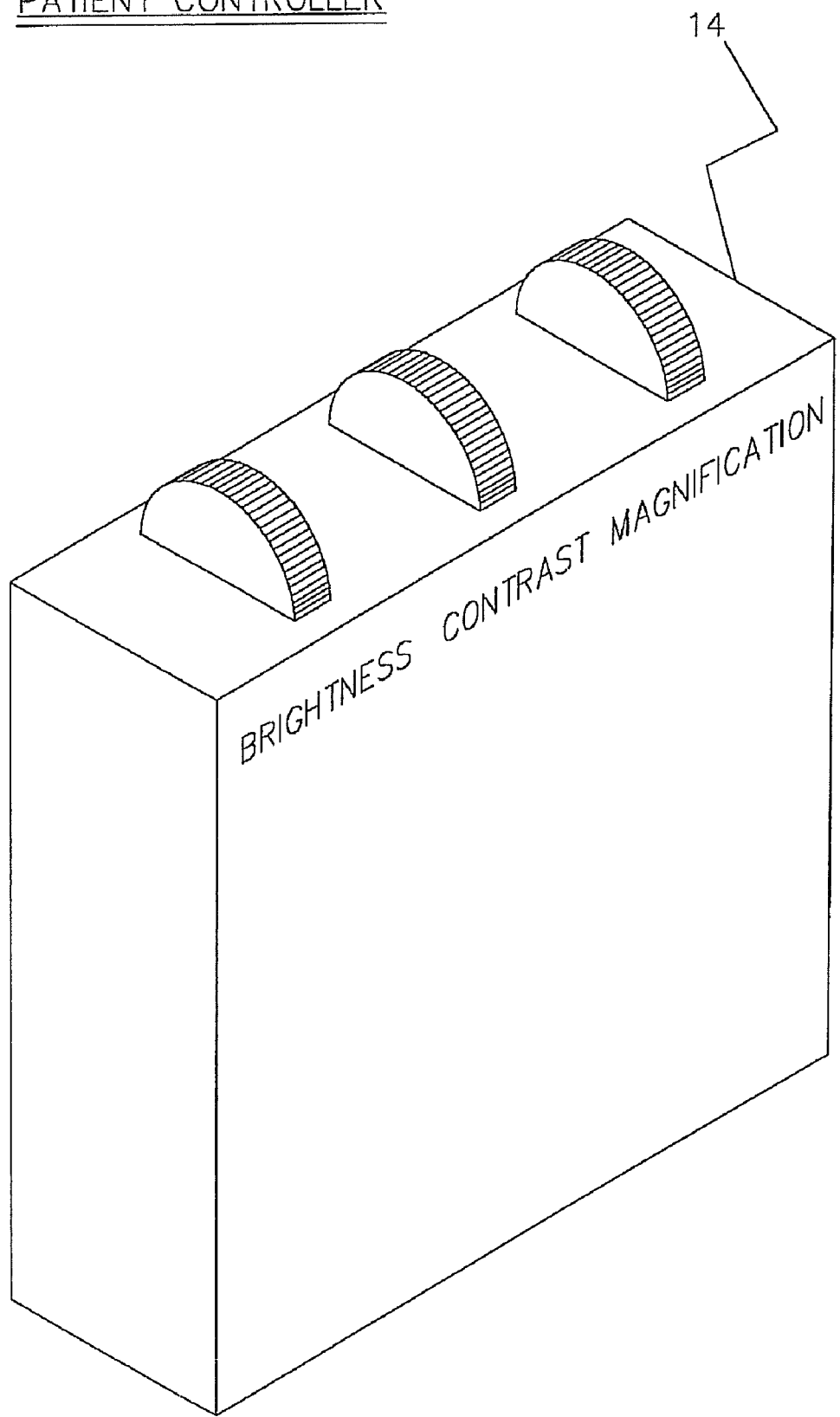
FIG. 20 shows the patient's controller unit.

Corresponding to the Physician's Local Controller, but with much less capability, is the Patient's Controller. FIG. 20 shows the patient's local controller unit. This unit can monitor and adjust brightness (2001), contrast (2002) and magnification (2003) of the image on a non-continuous basis. The magnification control (2003) adjusts magnification both by optical zoom lens control of the lens for the imaging means (FIG. 1, 111), and by electronic adjustment of the image in the data processor (FIG. 2, 113).

While the invention herein disclosed has been described by means of specific embodiments and applications thereof, numerous modifications and variations could be made thereto by those skilled in the art without departing from the scope of the invention set forth in the claims.

We claim:

1. An implantable device, comprising:
    an electrically non-conductive substrate;
    a plurality of electrically conductive straight feedthroughs through said electrically non-conductive substrate;
    a flip-chip circuit attached to said electrically non-conductive substrate using conductive bumps and electrically connected to a said plurality of electrically conductive straight feedthroughs; and
    a cover bonded to said electrically non-conductive substrate, said cover, said electrically non-conductive substrate and said electrically conductive straight feedthroughs forming a hermetic package.

2. The implantable device according to claim 1, wherein said electrically non-conductive substrate contains ceramic.

3. The implantable device according to claim 2, wherein said cover contains metal.

4. The implantable device according to claim 3, wherein said cover is brazed to said electrically non-conductive substrate.

5. The implantable device according to claim 1, further comprising a plurality of electrodes electrically coupled to said plurality of electrically conductive straight feedthroughs.

6. The implantable device according to claim 5, wherein said plurality of electrodes are bonded to said plurality of electrically conductive straight feedthroughs by insulated wires.

7. The implantable device according to claim 6, wherein said plurality of electrodes are suitable for stimulating tissue.

8. A method of making an implantable device, comprising:
    providing a ceramic containing non-conductive substrate defining a plurality of electrically conductive straight feedthroughs;
    brazing a metallic ring to said ceramic containing non-conductive substrate;
    electrically connecting a circuit to said electrically conductive straight feedthroughs by flip-chip attach; and
    welding a metallic top to said metallic ring.

9. The method according to claim 8, wherein said step of welding is laser welding.

10. An implantable device, comprising:
    an substantially planar electrically non-conductive substrate;
    a plurality of electrically conductive straight feedthroughs through said electrically non-conductive substrate forming electrodes;

a circuit attached to said electrically non-conductive substrate and electrically connected to said plurality of electrically conductive straight feedthroughs; and a cover bonded to said electrically non-conductive substrate, said cover, said electrically non-conductive substrate and said electrically conductive straight feedthroughs forming a hermetic package.

11. The implantable device according to claim 10, wherein an electrode is bonded to said electrically conductive straight feedthroughs.

12. The implantable device according to claim 10, wherein an electrode is electroplated to said electrically conductive straight feedthroughs.

13. The implantable device according to claim 10, wherein said circuit is a flip-chip circuit attached to said electrically non-conductive substrate using conductive bumps and electrically connected to said plurality of electrically conductive straight feedthroughs.

14. The implantable device according to claim 10, wherein said electrically non-conductive substrate contains ceramic.

15. The implantable device according to claim 14, wherein said ceramic comprises aluminum oxide.

16. The implantable device according to claim 14, wherein said ceramic comprises zirconium oxide.

17. The implantable device according to claim 10, wherein said cover contains metal.

18. The implantable device according to claim 10, wherein said cover is brazed to said electrically non-conductive substrate.

19. The implantable device according to claim 18, wherein said cover is brazed with a braze comprising Titanium.

20. The implantable device according to claim 18, wherein said cover is brazed with a braze comprising Nickel.

21. The implantable device according to claim 18, wherein said cover is brazed with a braze comprising gold.

* * * * *